United States Patent [19]

Hitzeman et al.

[11] Patent Number: 4,775,622
[45] Date of Patent: Oct. 4, 1988

[54] EXPRESSION, PROCESSING AND SECRETION OF HETEROLOGOUS PROTEIN BY YEAST

[75] Inventors: Ronald A. Hitzeman, Pacifica; David W. Leung, So. San Francisco, both of Calif.

[73] Assignee: Genentech, Inc., South San Francisco, Calif.

[21] Appl. No.: 438,236

[22] Filed: Nov. 1, 1982

Related U.S. Application Data

[63] Continuation-in-part of Ser. No. 355,297, Mar. 8, 1982, abandoned.

[51] Int. Cl.$^4$ .............. C12P 21/00; C12P 21/02; C12P 19/34; C12N 15/00; C12N 1/16; C12N 1/18
[52] U.S. Cl. ........................ 435/68; 435/70; 435/91; 435/172.1; 435/172.3; 435/255; 435/256; 435/320; 935/28; 935/37; 935/47; 935/48; 935/50; 935/69
[58] Field of Search ............... 435/68, 70, 91, 172.3, 435/255, 256, 317, 172.1, 317.1; 935/37, 47, 48, 69, 61

[56] References Cited

U.S. PATENT DOCUMENTS

| | | |
|---|---|---|
| 4,338,397 | 7/1982 | Gilbert et al. ............... 435/317 |
| 4,387,162 | 6/1983 | Aigle et al. ............... 435/255 |
| 4,414,150 | 11/1983 | Goeddel ............... 435/68 |
| 4,456,748 | 6/1984 | Goeddel ............... 435/91 |
| 4,546,082 | 10/1985 | Kurjan et al. ............... 435/172.3 |

FOREIGN PATENT DOCUMENTS

| | | | |
|---|---|---|---|
| 564690 | 8/1981 | Australia ............... 435/172.3 |
| 0020147 | 12/1980 | European Pat. Off. ......... 435/172.3 |
| 0043980 | 1/1982 | European Pat. Off. ......... 435/172.3 |
| 0067026 | 12/1982 | European Pat. Off. ......... 435/172.3 |
| 0068646 | 1/1983 | European Pat. Off. ......... 435/172.3 |

OTHER PUBLICATIONS

Botstein et al: Recomb. DNA Tech. Bull., 2, 49 (1979).
Davis et al: Nature, 283, 433 (1980).
Thorner: in *The Molecular Biology of the Yeast Saccharomyces*, Strathern et al (ed.), Cold Spring Harbor Labs, 1981, pp. 161–163.
Goeddel et al: Nature, 290, 20 (1981).
Sussman et al, "Pregrowth Hormone: Product of the Translation in Vitro of Messenger RNA Coding for Growth Hormone", Proc. Natl. Acad. Sci., U.S.A., 73: 29 (1976),
Webster's New Collegiate Dictionary, 1979, G. & C. Merriam Co., Springfield, Mass., p. 533.
Beach et al., "Nature", 290: 140–142 (12 Mar. 1981).
Taniguchi et al., "Proc. Natl. Acad. Sci. U.S.A.", 77(9): 5230–5233 (Sep. 1980).
Schekman et al. in The Molecular Biology of the Yeast Saccharomyces, Metabolism and Gene Expression, Strathern et al. (eds.), Cold Spring Harbor Laboratory, 1982, pp. 361–398.

*Primary Examiner*—James Martinell

[57] ABSTRACT

Yeast organisms are caused to express, process, and secrete protein that is normally heterologous to yeast and not required for its viability by transforming yeast with an expression vector containing a gene encoding heterologous protein and a signal sequence also heterologous to yeast.

19 Claims, 46 Drawing Sheets

Fig.1.

AMINO ACID SEQUENCES OF SECRETION SIGNALS

|  | -23 | -22 | -21 | -20 | -19 | -18 | -17 | -16 | -15 | -14 | -13 | -12 | -11 | -10 | -9 | -8 | -7 | -6 | -5 | -4 | -3 | -2 | -1 | +1 | +2 |
|---|---|---|---|---|---|---|---|---|---|---|---|---|---|---|---|---|---|---|---|---|---|---|---|---|---|
| Pre A | Met | Ala | Leu | Thr | Phe | Ala | Leu | Leu | Val | Ala | Leu | Leu | Val | Leu | Ser | Cys | Lys | Ser | Ser | Cys | Ser | Val | Gly | Cys | Asp |
| Pre D | Met | Ala | Ser | Pro | Phe | Ala | Leu | Leu | Met | Val | Leu | Val | Val | Leu | Ser | Cys | Lys | Ser | Ser | Cys | Ser | Leu | Gly | Cys | Asp |
| Pre D/A | Met | Ala | Ser | Pro | Phe | Ala | Leu | Leu | Met | Val | Leu | Val | Val | Leu | Ser | Cys | Lys | Ser | Ser | Cys | Ser | Val | Gly | Cys | Asp |
| Pre Y |  |  |  |  |  | Met | Lys | Tyr | Thr | Ser | Tyr | Ile | Leu | Ala | Phe | Gln | Leu | Cys | Ile | Val | Leu | Gly | Ser | Leu | Gly | Cys | Tyr |
| Pre β |  |  |  |  |  | Met | Thr | Asn | Lys | Cys | Leu | Leu | Gln | Ile | Ala | Leu | Leu | Leu | Cys | Phe | Ser | Thr | Thr | Ala | Leu | Ser | Met | Ser |

DdeI SITE IN DNA: between -10 and -9

CLEAVAGE SITE: between -1 and +1

THE INSERTION OF AN EcoRI SITE IN THE 5' FLANKING DNA
OF THE 3-PHOSPHOGLYCERATE GENE OF YEAST

Fig. 16.

DNA SEQUENCE OF THE 5' END
OF THE YEAST 3-PHOSPHOGLYCERATE KINASE
STRUCTURAL GENE AND FLANKING DNA

```
          -40       -30       -20       -10        -1  MET SER LEU SER SER LYS LEU LEU VAL
5'-------GATCATAAGGAAGTAATTATCTACTTTTACAACAAATATAAAACA ATG TCT TTA TCT TCA AAG TTG CTC GTC
```

EXPRESSION, PROCESSING AND SECRETION OF HETEROLOGOUS PROTEIN BY YEAST

CROSS REFERENCE TO RELATED APPLICATION

This is a continuation-in-part of application Ser. No. 06/355297, filed Mar. 8, 1982, now abandoned.

FIELD OF THE INVENTION

This invention is directed generally to recombinant DNA technology utilizing yeast host systems and expression vehicles that express, process and secrete heterologous protein as discrete product unaccompanied by unwanted presequence or other artifact of expression.

The discovery upon which this invention is based is the first instance where a protein normally heterologous to a yeast host is recoverable, in useful quantities, from the medium supporting the yeast culture, it having been expressed, processed and secreted the yeast organism in a manner mimicking its production in native cell environment. Thus, this invention results from the successful manipulation of expression vehicles and yeast host so as to direct the synthesis of protein not normally synthesized by the yeast host, and notably, to regulate the yeast host so as to cause the protein to come under direction of its secretory pathway. Thus, this invention is directed to the means and methods of obtaining useful quantities of heterologous protein from the medium of a yeast culture containing viable cells harboring expression vehicles containing DNA encoding the protein. Of enormous advantage is the enablement, by this invention, of obtaining useful, discrete protein product in the cell culture medium, eliminating resort to cell lysis in order to recover product hitherto only accessible from the cell contents, often in a form other than mature.

The publications and other materials referred to herein to illuminate the background of the invention, and in particular cases, to provide additional detail respecting its practice are incorporated herein by reference, and for convenience, are numerically referenced and grouped in the appended bibliography.

BACKGROUND OF THE INVENTION

Yeast organisms naturally transport a small number of certain homologous proteins to and sometimes through the plasma membrane as an essential contribution to cell surface growth and cell metabolism. As the cell buds as an incident of reproduction preparatory to formation of a daughter cell, additional proteins are required for formation of cell wall and plasma membrane as well as for metabolism. Some of these proteins must find their way to the site of function; hence, a secretory pathway is believed to exist (1). Certain homologous proteins involved in the above processes are formed by translation in the endoplasmic reticulum. Homologous proteins are those normally produced by the yeast species and required for its viability. Once formed, they migrate by enzymatic transfer to Golgi apparatus, thence within vesicles to plasma membranes where some associate, or to some extent, penetrate into the space between the plasma membrane and the cell wall. A small number of homologous proteins seems to be exported completely through the cell wall, such as α-factor and killer toxin (2,3).

Again, the bud region of the cell seems to be the site of attraction for the vesicles and by their fusion to the inner surface of the bud they contribute to the overall growth of the plasma membrane, and presumably, the cell wall (4,5,6). This theory provides no proof that secretion or migration of the protein(s) through the membrane actually occurs. Likewise, it is controversial still whether glycosylation of the protein may assist, or is implicated, in the so-called secretory process. Further, by definition "secreted" proteins are believed to have a signal prepeptide, postulated to be associated with the transport or incorporation process at the membrane surface. The function of such modifications of the mature protein, if any, in the secretory process and the overall role of the secretory pathway in surface growth are speculations not grounded in firm proof.

It was contemplated that recombinant DNA technology could provide valuable assistance in answering the open questions about the secretory process in yeast organisms and, given its proven applicability in enabling such, and other, organisms to produce copious quantities of heterologous polypeptide products endogenously (See, e.g., 7 to 17), in achieving appropriate manipulation of the yeast host so as to direct the secretion of heterologous protein in discrete, mature form.

SUMMARY OF THE INVENTION

This invention is based upon the discovery that yeast organisms can be caused to express, process and secrete protein that is normally heterologous to the yeast organism and not required for its viability such that the protein can be obtained from the medium supporting the viable, producing yeast cells in discrete form unaccompanied by unwanted polypeptide presequence or other artifact of expression. Suitable yeast cells in a viable culture are transformed with expression vehicles harboring DNA encoding a heterologous protein and a heterologous signal polypeptide. Upon expression of the protein together with the heterologous signal polypeptide, the expression product is processed and the mature heterologous protein is exported into the medium of the cell culture. The product is removed with relative ease from the medium, without need to disruptively disturb the viable yeast cells, and recovered in otherwise native form for use without need to remove unwanted presequence or other artifacts of expression (e.g., the methionine attached to the otherwise first N-terminus amino acid which is an expressional consequence of the AUG translational start signal codon). Thus, the medium can be obtained in a form substantially free of viable or disrupted (i.e., lysed or otherwise broken) cells and, given as it contains the desired product, is susceptible to more easily employed purification techniques. Such product, after purification, is fit for use as intended. For example, human leukocyte interferon product finds use as a human antiviral and/or antitumor agent (See, generally, 7 to 17).

In summary, the present invention comprises a protein normally heterologous to a yeast organism and not required for its viability, in discrete form unaccompanied by polypeptide presequence or other artifact of expression, as a product of yeast expression, processing and secretion as well as to the means and methods employed in producing such protein. Further, this invention provides yeast cultures capable of producing such protein and resultant yeast culture media containing such protein as product.

By the term "heterologous protein" as used herein is meant protein that is not normally produced by or required for viability of a yeast organism. This term contemplates the functional insertion of DNA encoding such protein, via recombinant DNA technology, into an expression vehicle, in turn used to transform a yeast organism host. Functional insertion of DNA connotes the insertion of DNA encoding the heterologous protein and presequence into an expression vector under control of expression directing promoter systems. Examples of such heterologous protein are hormones, e.g., human growth hormone, bovine growth hormone, etc.; lymphokines; enzymes; interferons, e.g., human fibroblast, human immune, and human and hybrid leukocyte interferons, etc.; viral antigens or immunogens, e.g., foot and mouth disease antigens, influenza antigenic protein, hepatitis core and surface antigens, etc.; and various other polypeptides, e.g., human serum albumin, human insulin, various glycoproteins, etc. "Heterologous presequence" or "heterologous signal polypeptide" refers to such polypeptides not normally produced or employed by a yeast system and may be selected from the signal polypeptide native to the heterologous protein under consideration or other heterologous (signal) polypeptide functionally linked to the heterologous protein under consideration.

"Secretion" as used herein means exportation of product through the plasma membrane and at least into or through the cell wall of the yeast organism into the medium supporting the cell culture. In this connection, it will be understood that in some instances, "secreted" product associates in some manner with the cell wall, perhaps necessitating a different purification procedure or a modification of the structure and function of the yeast host. "Processing" means the cellular, cleavage of the signal polypeptide from the mature protein so as to produce the protein unaccompanied by extraneous peptide in—so-called discrete—mature form. By extraneous peptide is included peptide artifacts of expression such as methionine, as noted above. Processing admits of inconsequential cleavage of the signal polypeptide at a locus not inactivatingly near the precise point of signal polypeptide union with mature protein.

BRIEF DESCRIPTION OF THE DRAWINGS

FIG. 1 depicts a comparison of the amino acid sequence of the signal prepeptide of human IFN-α1 (pre D), IFN-α2 (pre A), IFN-α1,2 (pre D/A), IFN-γ (pre γ), and IFN-β (pre β). The amino acids underlined represent differences between the amino acid sequences of pre A and pre D. The DdeI site indicates the junction of the D and A presequences in preparation of the hybrid pre D/A presequence.

FIG. 16 illustrates the 5'-flanking sequence plus the initial coding sequence for the PGK gene before insertion of an XbaI and EcoRI sites.

DETAILED DESCRIPTION

Materials

Figure 2:
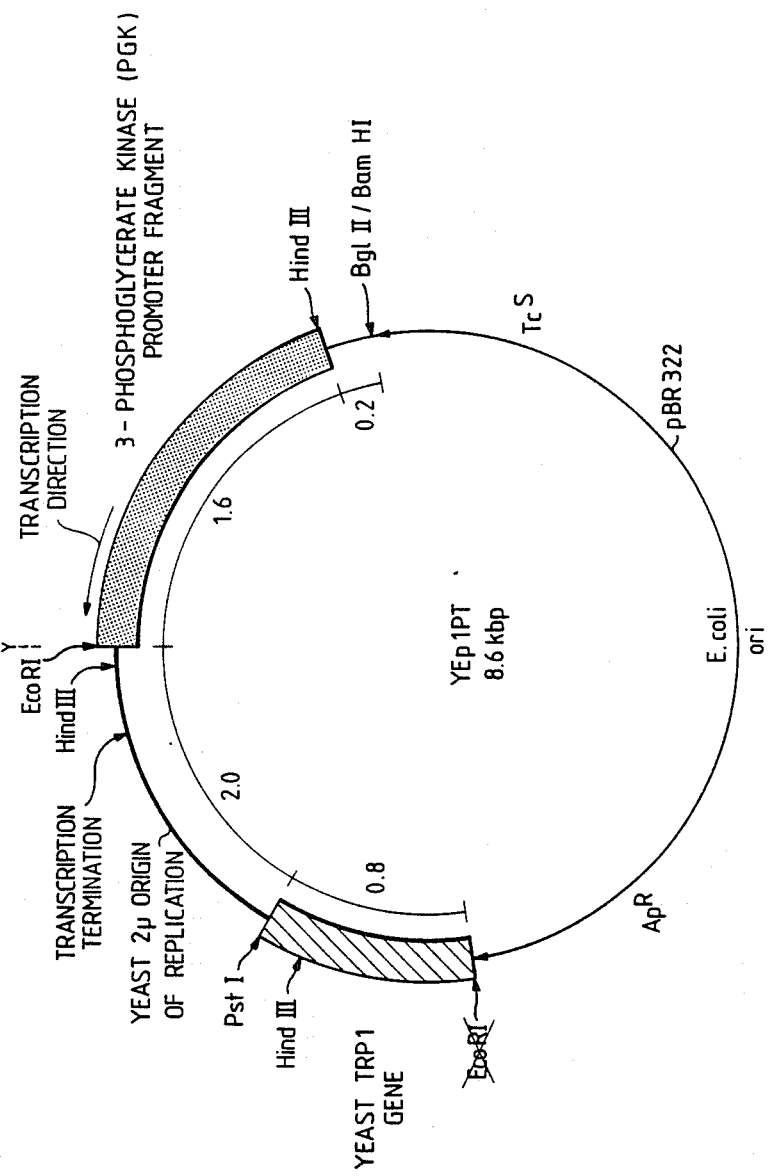
FIG. 2 is a diagram of the yeast expression plasmid YEpIPT, used herein as a general vehicle for expression of various gene inserts, showing some of its restriction sites and various regions of interest.

All DNA restriction and metabolism enzymes were purchased from New England Biolabs and from Bethesda Research Laboratories. DNA restriction enzyme and metabolic enzymes were used in conditions and buffers described by their respective manufacturers. ATP and the deoxynucleotide triphosphates dATP, dGTP, dCTP and dTTP were purchased from PL Biochemicals. DNA linkers were made by standard methods.

DNA Preparation and Transformation

Purification of covalently closed circular plasmid DNAs from E. coli (18) and transformation of E. coli

(19) were done in accordance with previously described procedures. *E. coli* miniscreens were as described by (20). Transformation of yeast was done as previously described (21), however with the following modifications. Two hundred ml of cells were used at $2 \times 10^7$ cells/ml and washed with 25 ml H$_2$O by centrifugation. These cells were treated with 10 ml of 1M sorbitol, 25 mM EDTA (pH=8) and 50 mM dithiothreitol for 10 min at 30° C. followed by a 10 ml wash of 1M sorbitol. Pelleted cells were then gently resuspended in 10 ml of SCE (1M sorbitol, 0.1M sodium citrate, pH=5.8, and 0.01M EDTA) and treated at 30° C. with 200 μg of zymolyase 60,000 (Kirin Brewery). Spheroplasting was followed to 80 percent by adding 100 μl of the suspension to 0.9 ml of 10 percent SDS and measuring Abs$_{800}$ mμ, using a dilution of cells before adding the enzyme as 0 percent (lysis in the 10 percent SDS results in a drop in Abs$_{800}$). The cells were then washed 3X with 10 ml of 1M sorbitol. Cells can be stored several days at 0° C. in the sorbitol. The cells were then washed once with 1M sorbitol, 10 mM CaCl$_2$, and 10 mM Tris-HCl (pH 7.4) and then resuspended in 1 ml of the same. Five to 15 μg of purified plasmid DNA or 20 μl of *E. coli* derived miniscreen DNA (2/5 of the plasmid DNA from a 5 ml stationary culture of *E. coli* grown in LB) were then added and gently mixed with 100 μl of the resuspended cells for 15 min. Then 1 ml of a solution containing 20 percent (w/v) polyethylene glycol 4000 (Baker), 10 mM CaCl$_2$, and 10 mM Tris-HCl (pH 7.5) was added with gentle mixing for 15 min. The cells were then centrifuged down and gently resuspended in 200 μl SOS (1M sorbitol, 33.5 percent (v/v) YEPD broth, and 6.5 mM CaCl$_2$) and incubated at 30° C. for 20 min. One hundred μl of this suspension was then placed on a Petri plate containing 20 ml of bottom agar (182 g sorbitol, 20 g glucose, 6.7 g YNB, and 30 g Difco agar per liter of H$_2$O) and covered with 10 ml of 50° C. top agar (same as bottom agar but with 1 ml of adenine (1.2 mg/ml), 1 ml uracil (2.4 mg/ml), and 1 ml of -trp drop-out mix per 50 ml of bottom agar [-trp drop-out mix contains these amino acids per 100 ml of H$_2$O: 0.29 arg, 0.1 g his, 0.6 g ile, 0.6 g leu, 0.4 g lys, 0.1 g met, 0.6 g phe, 0.5 g thr]. This Trp+ selection results in $10^3$ to $10^4$ yeast transformants per μg plasmid DNA.

Yeast plasmid was obtained from yeast by growing 15 ml of yeast to stationary phase (Abs$_{660}$=5-6) in YNB+CAA (see *Strains and Media, infra*), by spheroplasting as in the procedure above, by pelleting of cells, and by using the *E. coli* miniscreen procedure (without lysozyme) as described by (20).

Stability of plasmids in yeast was determined by diluting cells during selective growth in YNB+CAA and plating on YEPD plates (nonselective). After 2 days growth at 30° C., these plates were replica plated to YNB+CAA plates (Trp+ selection). Percent plasmid stability was calculated by number of colonies that grow nonselectively minus those that don't grow selectively divided by number of colonies grown nonselectively times 100.

Strains and Media

*E. coli* K-12 strain 294 (ATCC no. 31446) (22) was used for all other bacterial transformation. Yeast strains pep4-3 (20B-12, d trp1 pep4-3) (23) and GM3C-2 (α, leu 2-3, leu 2-112, trp 1-1, his 4-519, cyc 1-1, cyp 3-1) (24) were used for yeast transformations. Yeast strains 20B-12 and GM3C-2 have been deposited without restriction in the American Type Culture Collection, ATCC Nos. 20626 and 20625, respectively, each on 5 Mar. 82. Various yeast strains can be employed—see Lodder et al., *The Yeasts, a Taxonomic Study*, North-Holland Publ. Co., Amsterdam. Similarly various media can be employed—*Difco Manual of Dehydrated Culture Media and Reagents for Microbiological and Clinical Laboratory Procedures*, 9th Ed., Difco Laboratories, Inc., Detroit, Mich.(1953).

LB was as described by Miller (25) with the addition of 20 μg/ml ampicillin (Sigma) after media is autoclaved and cooled. Yeast were grown on the following media: YEPD contained 1 percent yeast extract, 2 percent peptone and 2 percent glucose ±3 percent Difco agar. YNB+CAA contained 6.7 grams of yeast nitrogen base (without amino acids) (YNB) (Difco), 10 mg of adenine, 10 mg of uracil, 5 grams Difco casamino acids (CAA), 20 grams glucose and ±30 grams agar per liter (used for Trp+ selection).

Growth Curve and Extract Preparation

Individual colonies of yeast strains YEpIPT-preLeIF-A 53t/pep4-3 and YEpIPT-LeIF-A 1/pep4-3 were grown for 7 hours at 30° C. in 100 ml YNB+CAA to an A$_{660}$ of approximately 1.1. One hundred milliliters of these cultures were diluted to 1 liter with YNB+CAA to give a solution with A$_{660}$ of 0.1. These 1 l cultures were then grown at 30° C. and 10 ml aliquots were drawn periodically to measure optical density, interferon production and secretion. For assay each 10 ml aliquot was centrifuged at 7K rpm for 15 minutes in a Sorval RC3B. The supernate (media) was assayed without dilution. The cells were resuspended in 0.4 ml 7M guanidine-HCl containing an equal volume of glass beads and vortexed twice for 2 minutes at high speed. The cell lysate was then diluted into PBS/BSA (150 mM NaCl, 20 mM sodium phosphate (pH=7.9), and 0.5 percent bovine serum albumin) for bioassay.

Interferon Assays

Extracts of yeast were assayed for interferon by comparison with interferon standards by the cytopathic effect (CPE) inhibition assay (26). Yeast extracts were prepared as follows: Ten ml cultures were grown in YNB+CAA until reaching A$_{660}$≃1-2. Cells were collected by centrifugation, then resuspended in 3 ml of 1.2M sorbitol, 10 mM KH$_2$PO$_4$, pH=6.8 and 1 percent zymolyase 60,000, then incubated at 30° C. for 30 min (to 90 percent spheroplasting). Spheroplasts were pelleted at 3000 xg for 10 min., then resuspended in 150 μl of 7M guanidine hydrochloride (GHCl) plus 1 mM phenylmethylsulfonylfouride (PMSF). Extracts were diluted 20 to 100 fold in PBS/BSA buffer (20 mM NaH$_2$PO$_4$, pH=7.4, 150 mM NaCl, 0.5 percent BSA) immediately before the assay. Alternatively, 10 ml of cells at the same A$_{660}$ were pelleted and resuspended in 0.4 ml of 7M GHCl in an Eppendorf (1.5 ml) tube containing about 0.4 ml of glass beads (0.45 to 0.5 mm, B. Braun Melsurgen AG). These tubes were vortexed 2x for 2 min at highest vortex setting, keeping on ice in between. The extracts were centrfigued 0.5 min. in Eppendorf centrifuge and diluted in PBS/BSA buffer as above. Bioassays were performed with MDBK cells (26) for LeIF A, LeIF D, and the pre-forms; but with HeLa cells (26) for IFN-γ and preIFN-γ.

Purification of (pre D/A) LeIF A from the Media

A single colony of yeast strain YEpIPT-preLeIF-A 53t/pep4-3 was grown at 30° C. in 500 ml YNB+CAA to an $A_{660}$ of 2.4. Five hundred milliliters of this culture was diluted to 5L with YNB+CAA to give an $A_{660}$ of 0.21; the resultant 5L culture was grown at 30° C. until $A_{660}=4$. At this time the 5L culture was harvested by centrifugation at 7,000 rpm for 10 minutes. Ten milliliter aliquots were withdrawn periodically during the fermentation to measure optical density, interferon production and secretion. Before assay, each aliquot was centrifuged for 5 minutes in a bench-top refrigerated centrifuge to separate the cells from the media. The medium and cells were assayed as described above (See FIGS. 9, 10A, 10B).

The medium was concentrated to a final volume of 200 ml and then diafiltered against tris/cys/EDTA, pH 8.0 on a 1000 dalton ultrafiltration membrane (0-PS, Osmonics) in an Amicon thin channel apparatus (TCF 10). The retentate (200 ml) was passed over a 1.5 ml immunoaffinity column containing a monoclonal antibody to LeIF-A covalently bound to Affigel 10 (BioRad) at a flow rate of 15 ml/hour. More than 80 percent of the interferon activity in the original solution bound to the column. The flow-through was then reapplied to the column at a flow rate of 40 ml/hour. Following the second application, approximately 7 percent of the original interferon activity was found in the flow through. The column was then washed with 0.2M NaCl in tris/cys/EDTA, pH 8.0. Approximately 1.7 percent of the activity was eluted during this wash.

Figure 11:
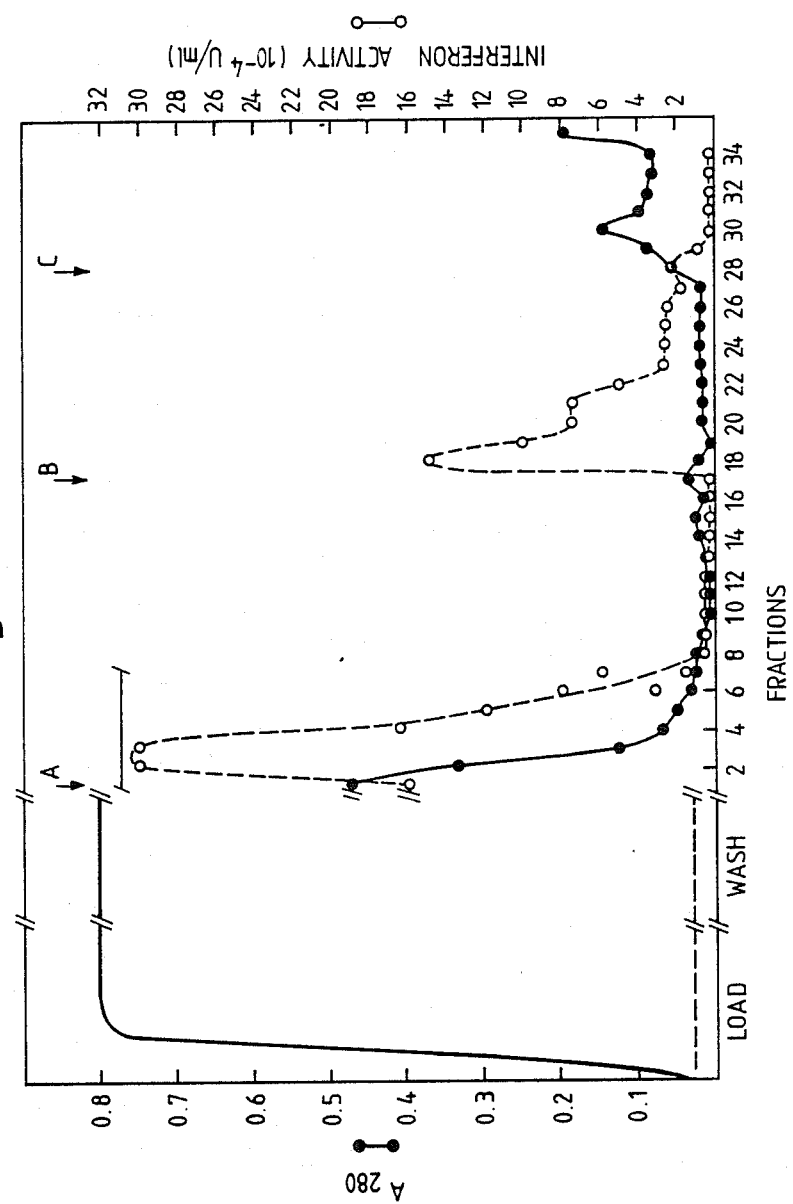
FIG. 11 is an elution profile of media pre D/A LeIF from a monoclonal antibody column.
Figure 12:
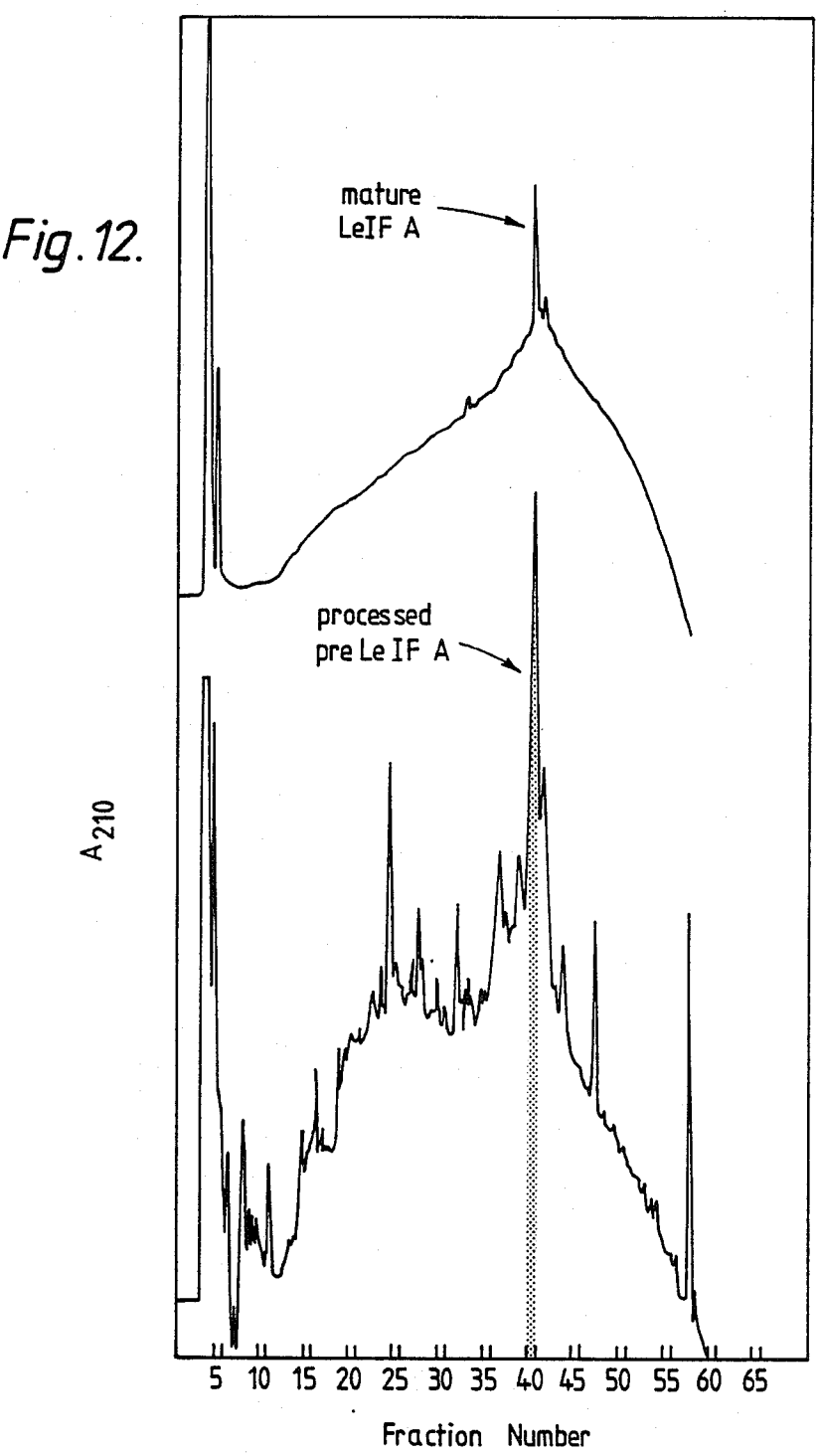
FIG. 12 is the HPLC tracing of the peak A interferon pool from the monoclonal antibody column.

The bulk of the interferon activity (approximately 50 percent of the original activity) was then eluted from the column with 51.5 ml pH 5.5 deionized water. The column was finally washed with 22.5 ml 0.2M acetic acid to elute any remaining protein; approximately 8 percent of the original activity was eluted. Following the acetic acid elution, the column was re-equilibrated with tris/cys/EDTA, pH 8.0. Fractions of 2.25-4.5 ml were collected during the water, acetic acid and tris/cys/EDTA washes (FIG. 11). Fraction numbers 1-7 were pooled and lyophilized to dryness. The residue was redissolved in 200 ul percent trifluoroacetic acid (TFA), pH 2.5 and further purified by HPLC on a Synchropak RP-P column. The column was eluted at a flow rate of 1 ml/minute with a linear gradient of 0 to 100 percent acetonitrile in 0.1 percent TFA, pH 2.5. One milliliter fractions were collected and assayed following dilution into PBS/BSA as described above. A 2.5 μg sample of purified IFN-A was also chromatographed as a control (FIG. 12). The interferon activity eluted from the column as a single peak centered around fraction 39. This fraction was lyophilized to dryness and the residue sequenced.

Sequence Analysis

Sequence analysis was based on the Edman degradation (27). The sample was introduced into the cup of a Beckman 890B spinning cup sequencer. Polybrene TM (poly N,N,N$^1$N$^1$-tetraymethyl - N-trimethylenehexamethylene diammonium diacetate) was used as a carrier in the cup (28). The sequencer was modified with a cold trap and some program changes to reduce background peaks. The reagents were Beckman's sequence grade 0.1 molar Quadrol buffer, phenylisothiocyanate, and heptafluorobutyric acid.

A modification also included automatic conversion of the 2-anilino-5-thiazolinone derivatives as they were extracted from the sequencer. The 1-chlorobutane was collected in a Pierce Reacti-Vial TM and dried under nitrogen. Then 25 percent trifluoroacetic acid (TFA) in water was added to the 2-anilino-5-thiazolinone and heated to 20° C. for 10 min to convert it into the 3-phenyl-2-thiohydantoin (PTH derivative) (29). The PTH-amino-acid residue was then automatically dissolved in 50 percent acetonitrile and water and injected into a reverse-phase high-pressure liquid chromatograph. Each PTH-amino acid was then identified by comparison to the retention times of a standard mixture of PTH-amino acids that was introduced into the conversion vial and treated the same way as a cycle from the sequencer. Results are summarized in FIG. 13 and discussed infra.

Western Blotting Procedure

Proteins were first subjected to electrophoresis on a polyacrylamide slab gel in the presence of sodium dodecyl sulfate (46,47) before electrophoretic transfer to nitrocellulose paper (S+S BA 85) and subsequent immunological identification of HGH. The transfer apparatus (Electroblot, E.C. Apperatus Corp., St. Petersburg, FL.) was assembled after the gel and nitrocellulose paper had been washed briefly with a transfer buffer containing 25 mM Tris, 192 mM glycine, pH 8.4. The transfer was carried out at 400ma. for 1.5 hrs., after which the blot was placed in 50 mM Tris pH 7.4, 0.15M NaCl, 5 mM EDTA, 0.25 percent gelatin (w/v), 0.05 percent NP-40 and agitated gently overnight. An appropriate dilution of rabbit anti-human hGH antiserum was placed in a plastic bag with the blot and NP-40/gelatin buffer (typically 100 μl/cm$^2$) and incubated 2 hrs. at room temperature with gentle rocking. The blot was washed briefly with H$_2$O followed by NP-40/gelatin for 1 hr., and probed with [125I]Protein A (New England Nuclear) diluted into NP-40/gelatin buffer in a Seal-a-Meal bag for 1 hr. at room temperature with gentle rocking. After washing several times with H$_2$O, the blot was wrapped in cellophane and placed in a cassette overnight with X-Omat-AR film (Kodak) with an intensifying screen at −70° C.

Gel Staining

Polyacrylamide gels containing protein were stained by the method of Oakley et al. (41).

Secretion signal sequences of mammalian interferon genes

With the recent isolation of cDNAs containing the genes for leukocyte (7), fibroblast (10), and immune (30) interferons and the recent development of yeast as an expression system for heterologous genes (14), it became possible to test the expression of heterologous genes containing coding regions for signal peptide sequences in yeast.

FIG. 1 shows the signal sequences for five different interferons. These amino-terminal sequences are believed to facilitate the secretion of interferon proteins from mammalian cells. During the process the signal sequence is removed by specific protease cleavage, between position −1 and +1 to give what is known as the mature form of the interferon. These sequences have general characteristics of other secretion signal sequences (31). They all are very hydrophobic, about the same length as other signals, and have a small amino acid to the left of the cleavage site. Although preLeIFA, preLeIFD, and PreIFN-γ all cleave between glycine and cysteine this is not a general rule for other mammalian signals as evidenced by preIFN-β.

Indeed there is no consensus signal sequence among organisms or within the same organism. There is also no consensus sequence at the cleavage point between the signal sequence and the mature form of the protein product.

Therefore, it was of great interest to attempt the expression of these pre-interferons in yeast to determine whether these heterologous proteins would be secreted from yeast and what the nature of processing of these proteins might be. Although yeast is a eukaryotic organism like mammalian cells and although yeast appears to have a secretion pathway similar in many respects to higher eukaryotes (1,32), it is a very primative eukaryote and the proper function and processing of these gene products would require a great conservation of process between yeast and mammalian cells during evolution, the results of which are not at all apparent.

Construction of a yeast plasmid for expression of the pre-interferon genes

Information for the construction of a plasmid for the expression of a heterologous gene in yeast has been published (14).

The plasmid used in this work is shown in FIG. 2. This plasmid contains a portion of pBR322 (33) with the ampicillin resistance (Ap$^{Rl}$) gene and the E. coli origin of replication for selection and stable growth in E. coli (used as an intermediate between in vitro construction and transformation of yeast). The plasmid also contains the TR1 gene on an EcoRI to PstI fragment which originates from chromosome III of yeast (34-36). This gene allows for selection in trp1-yeast and thus can be used to isolate yeast cells containing the plasmid and for maintainence of the plasmid. Furthermore the plasmid contains a yeast origin of replication on a 2.0 kbp fragment from endogenous yeast 2μ plasmid DNA (37). This origin allows the DNA to replicate autonomously in yeast and be maintained as a plasmid.

The other main component of the system is the yeast 3-phosphoglycerate kinase (PGK) promoter fragment which originates transcription near the only EcoRI site in the plasmid (the other EcoRI site was removed by filling in the restricted site using E. coli DNA polymerase I (Klenow) followed by the blunt end ligation).

The isolation of the 3-phosphoglycerate kinase (PGK) gene has been discussed elsewhere (37a) as well as the construction of the 1.5 kbp promoter fragment (infra). A Hind III/Bgl II fragment from the yeast TRP 1 gene region (34-36) of chromosome III was used as a convertor of Hind III to Bgl II for ligation with the Bam HI site of pBR322, making the plasmid tetracycline sensitive (Tc$^S$). Furthermore, it should be mentioned that the 2.0 kbp fragment from 2μ DNA performs another function in that it contains a transcription termination/polyadenylation signal which is normally the termination signal for the "Able" gene in 2μ plasmid (37). Such a region appears to be essential for good expression. Gene inserts as EcoRI fragments in the right orientation can then be expressed as protein when the vector is put into yeast.

Construction of yeast plasmids for the expression of the various interferon genes The yeast expression plasmid YEpIPT contains a single EcoRI restriction site. Insertion of a foreign gene into this unique EcoRI site leads to the expression of this gene under the control of the yeast phosphoglycerate kinase (PGK) promoter. A convenient way to insert the various interferon genes into the EcoRI site of this yeast plasmid is to have DNA fragments with EcoRI sites flanking the initiation codon and the termination codon of the various interferon genes. We describe here the construction of such EcoRI fragments for the expression of interferon genes. It is important to use converters to EcoRI at the 3'-end of the gene so they do not terminate transcription but allow transcription through to the 2μ terminator.

We described previously the construction of an EcoRI site just preceding the ATG initiation codon for the mature IFN-α1 gene (14,17), the mature IFN-α2 gene (7), the mature IFN-β gene (10), and the mature IFN-γ gene (30).

DNA restriction analysis shows there is an EcoRI site conveniently located in the 3'-noncoding region of the cDNA clone of IFN-α1 (8), thus digestion of the plasmid pLeIFD3 (17) with EcoRI generates a 583 bp EcoRI fragment, which contains the entire IFN-α1 gene.

Figure 3:
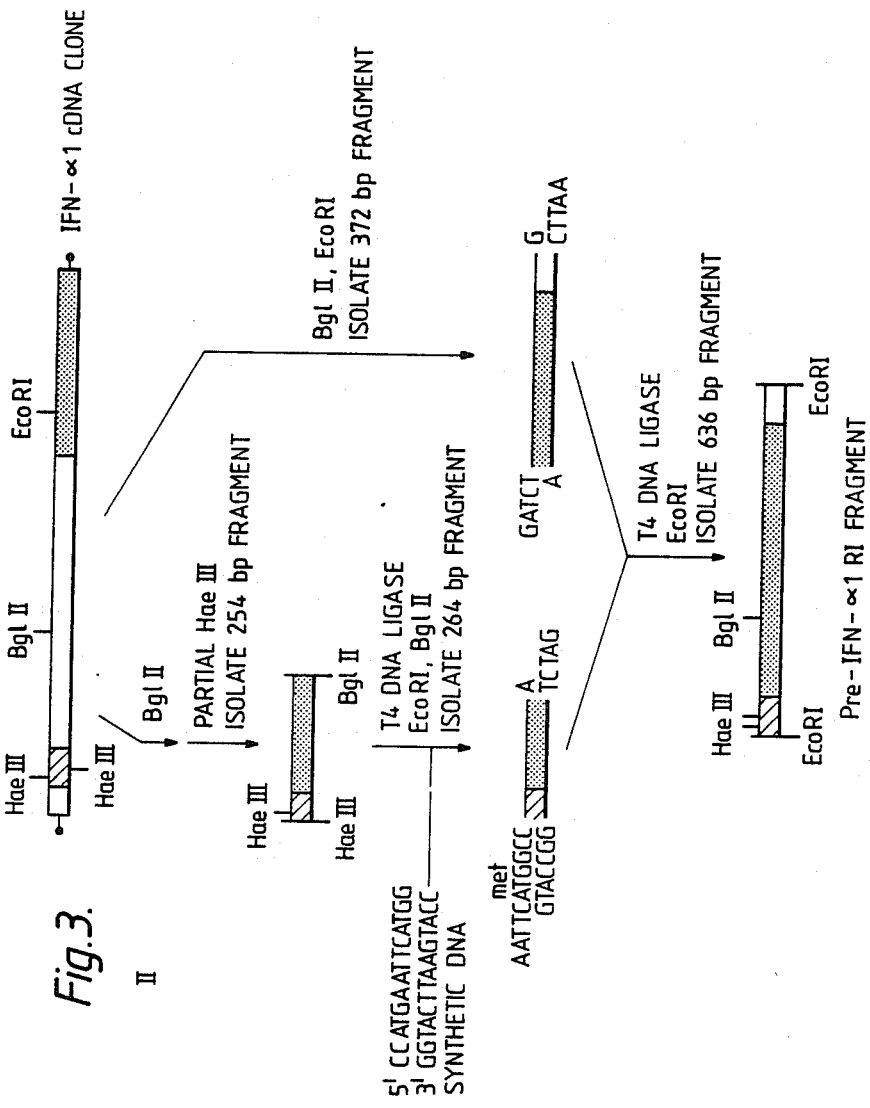
FIG. 3 shows the construction of an EcoRI fragment containing the pre-plus IFN-α1 gene for direct expression of IFN-α1 in yeast.

FIG. 3 shows the construction of a EcoRI fragment containing the pre-IFN-α1 gene. A HaeIII site is located between the first and second amino acid of pre-IFN-α1 (8). A partially HaeIII digested 254 bp fragment that extends from this HaeIII site to the BglII site in the middle of the coding region was isolated. A self-complementary synthetic oligonucleotide 5'-CCAT-GAATTCATGG-3', was blunt-end ligated to the 254 bp HaeIII-BglII fragment in order to generate an EcoRI site preceding the ATG initiation codon. A 264 bp EcoRI-BglII fragment was then isolated by digesting the ligation mixture with EcoRI and BglII. This EcoRI-BglII fragment, which contains the front half of the preIFN-α1 gene, was then ligated to the back half of the pre-IFN-α1 gene, a 372 bp BglII-EcoRI fragment isolated from digestion of the IFN-α1 cDNA clone with BglII and EcoRI. The EcoRI fragment containing the entire pre-IFN-α1 gene was then generated by digesting the ligation mixture with EcoRI and isolating a 636 bp fragment.

Figure 4:
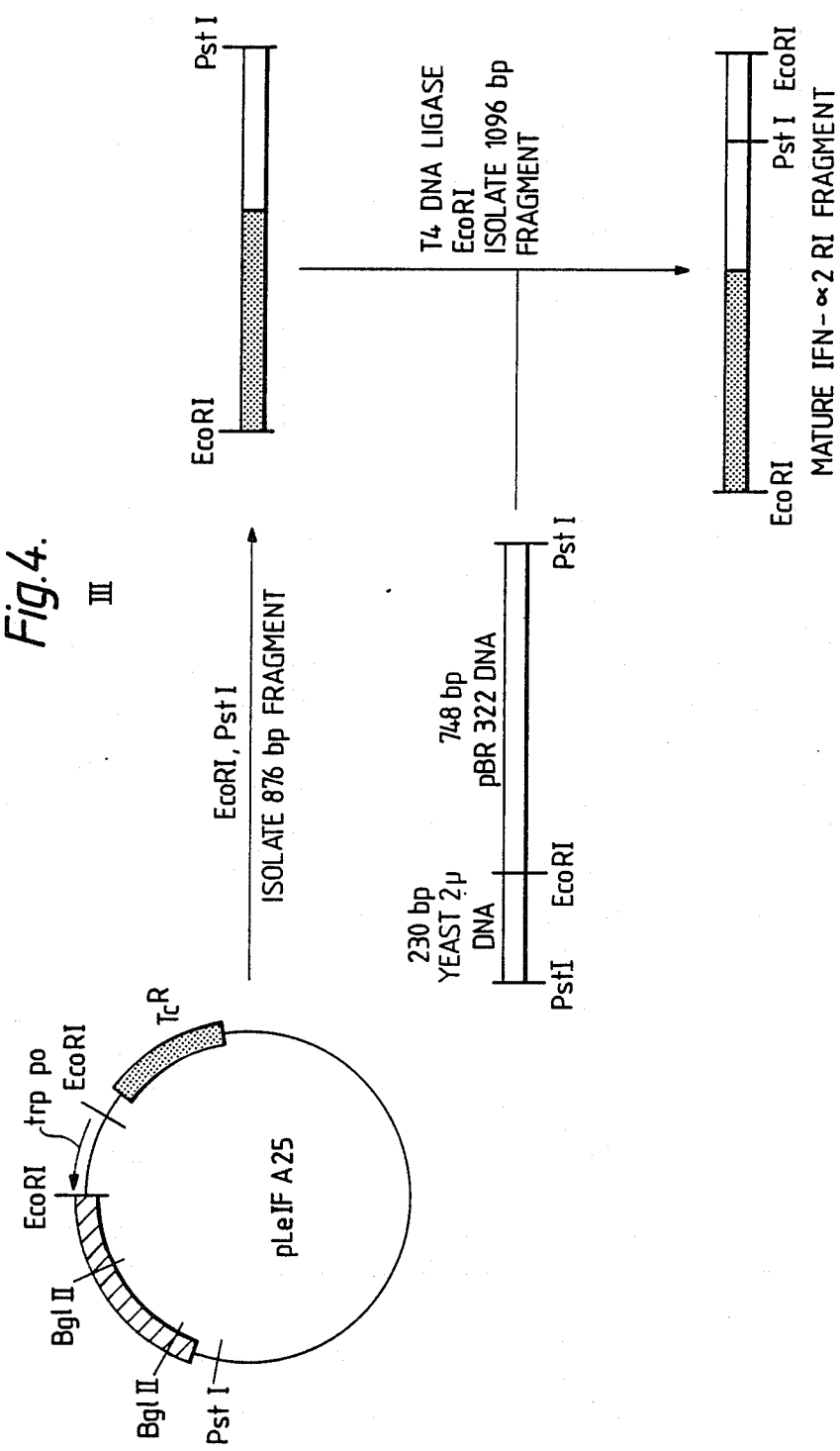
FIG. 4 show the construction of an EcoRI fragment containing the mature IFN-α2 gene for direction expression in yeast.

FIG. 4 shows the construction of an EcoRI fragment containing the mature IFN-α2 gene. A 876 bp EcoRI-PstI fragment that contains the mature IFN-α2 gene with an EcoRI site just preceding the ATG initiation codon and with 400 bp of 3'-noncoding region derived from the cDNA clone was isolated by digesting the plasmid pLeIFA25 (7) with EcoRI and PstI. The PstI end of this 876 bp fragment was then converted to an EcoRI site by using an adaptor fragment. This 978 bp adaptor fragment contains an internal EcoRI site and has PstI sites on both ends. 230 bp of this fragment that extends from one Pst end to the EcoRI site derives from the yeast plasmid 2μ DNA (37). 748 bp of the rest of the fragment that extends from the EcoRI site to the other PstI end derives from the bacterial plasmid pBR322 (the entire fragment being derived from YEp13 (37(b)). Ligation of this adaptor fragment to the 876 bp EcoRI-PstI fragment containing the mature IFN-α2 gene followed by subsequent digestion with EcoRI generates a 1096 bp fragment containing the mature IFN-α2 gene with EcoRI sites on both ends.

Figure 5:
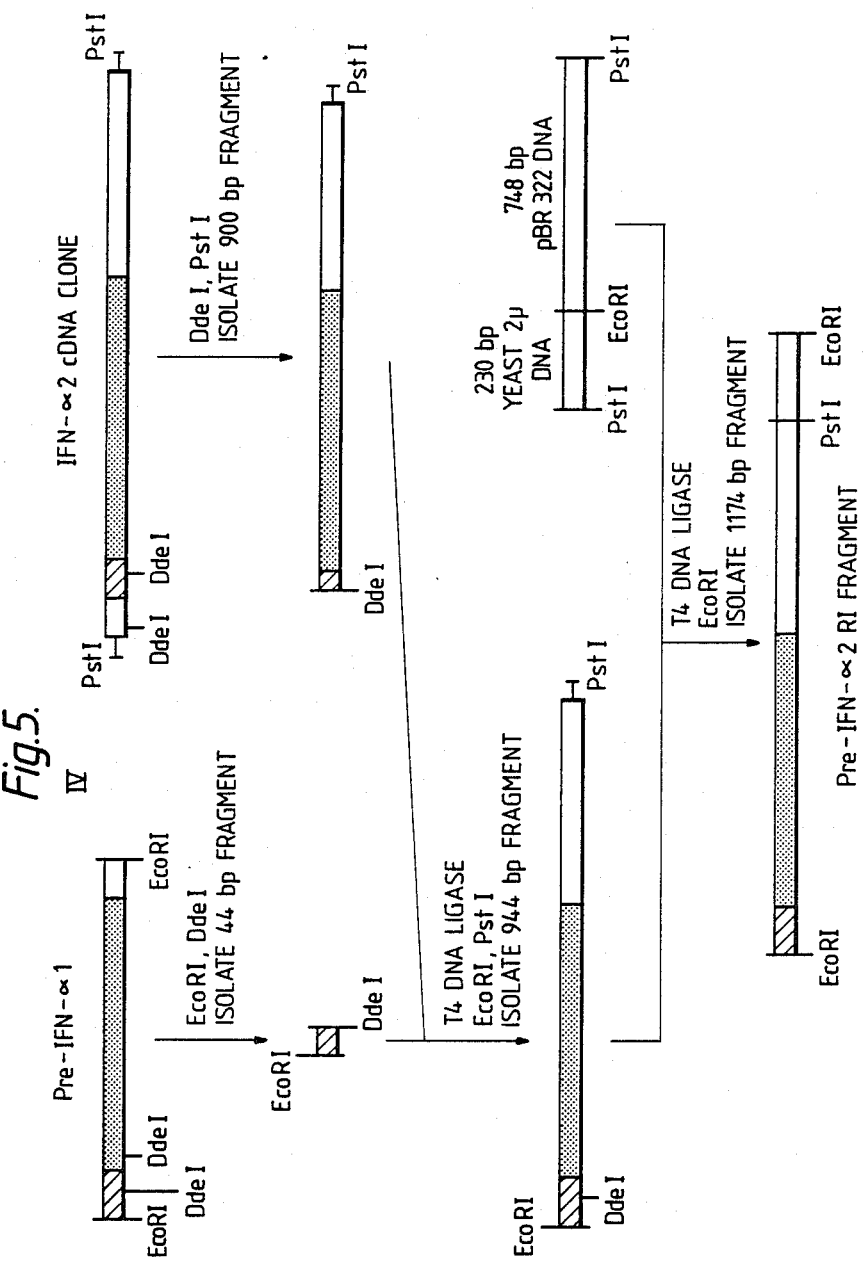
FIG. 5 shows the construction of an EcoRI fragment containing the pre-plus IFN-α2 gene with the coding sequence of the first 14 amino acids in the presequence of pre-IFN-α1, for direct expression of IFN-α2 in yeast.

FIG. 5 shows the construction of an EcoRI fragment containing the pre-IFN-α2 gene. Restriction analysis shows a common DdeI site present between the 14th and the 15th amino acid in the presequence of both pre-IFN-α1 and 2 genes. Ligation of the 44 bp EcoRI-DdeI fragment derived from the EcoRI fragment coding the pre-IFN-α1 gene and the 900 bp DdeI-PstI fragment derived from the cDNA clone of IFN-α2 followed by subsequent digestion with EcoRI and PstI generates a 944 fragment. This 944 bp EcoRI-PstI fragment contains the coding sequence of the first 14 amino acids in the prepeptide derived from IFN-α1, the coding sequence of the rest of the prepeptide, and the entire mature protein derived from IFN-α2. The PstI end of this 944 bp fragment was then converted to an EcoRI site using the adaptor fragment as in the case of the construction of an EcoRI fragment for mature IFN-α2.

Figure 6:
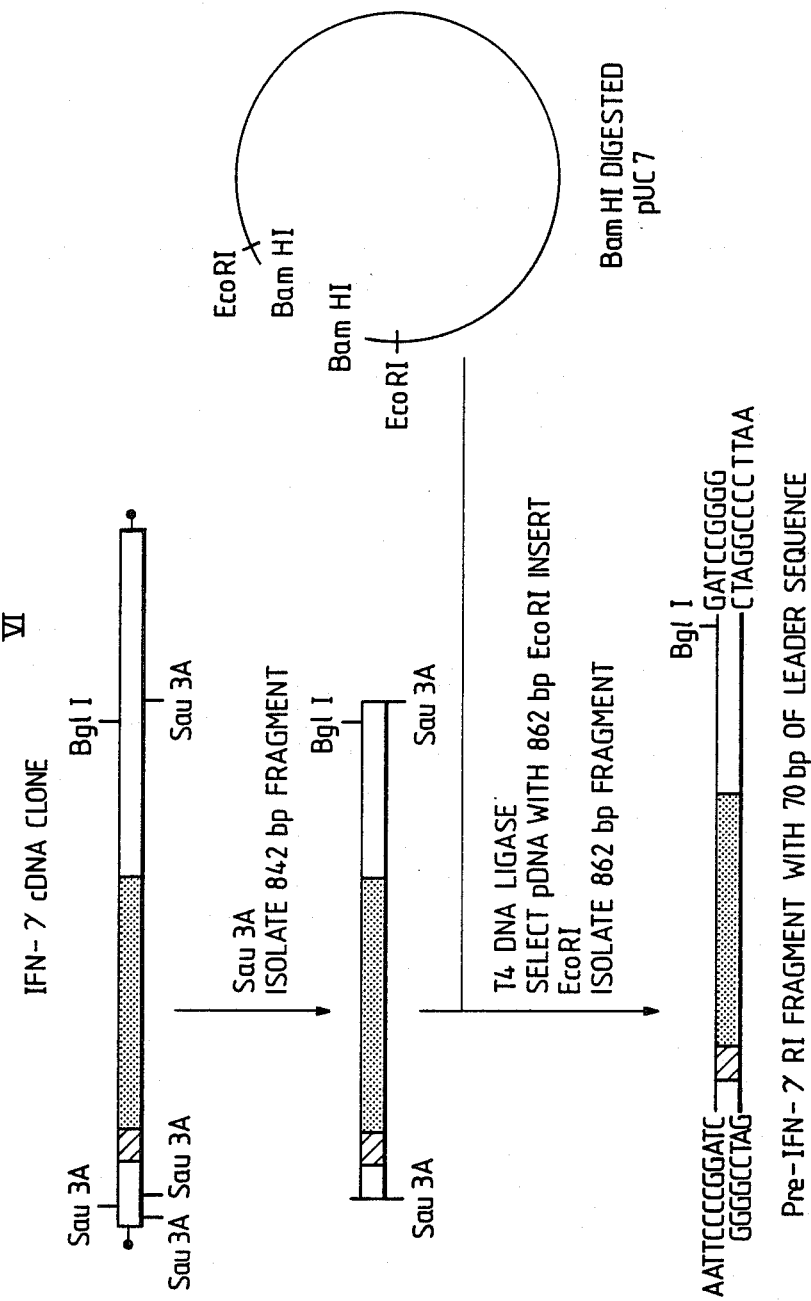
FIG. 6 shows the construction of an EcoRI fragment containing the pre-plus IFN-γ gene with 70 bp of leader sequence preceding the initiation ATG codon for expression of IFN-γ in yeast.

FIG. 6 shows the construction of an EcoRI fragment containing the pre-IFN-γ gene with 70 bp of leader sequence preceding the initiation ATG codon. Digestion of the IFN-γ cDNA clone (30) generates a 842 bp Sau3A fragment with 60 bp of 5'-flanking sequence, the entire coding sequence of pre-IFN-γ and 290 bp of 3'-noncoding sequence. This Sau3A fragment was then cloned into a BamHI digested vector pUC7, a plasmid counterpart of the single stranded phage M13mp7 (38). The plasmid pUC7 was derived from pBR322 by first removing the 2,067 base-pair EcoRI-PvuII fragment containing the tetracycline resistance gene, then inserting a 425 base-pair HaeII fragment from the phage M13 derivative mP7 (38) into the HaeII site of the resulting plasmid at position 2352 (relative to the pBR322 notation). The HaeII fragment from mp7 contains the N-terminal coding region of the *E. coli* lacZ gene in which a multi-restriction enzyme cloning site of the sequence has been inserted between the 4th and 5th amino acid residues of β-galactosidase. Insertion of a foreign DNA fragment into these cloning sites disrupts the continuity between the lac promoter and lacZ gene, thus altering the phenotype of a JM83 transformed with the plasmid from lac+ to lac−. As there are two EcoRI sites flanking the BamHI sites in the multi-restriction cloning site of pUC7, digesting the plasmid containing the 842 bp Sau3A insert with EcoRI would give an 862 bp fragment containing the entire pre-IFN-γ sequence flanked by EcoRI sites.

Digestion of the plasmid pIFN-γtrp48 (30) with EcoRI and BglI generates a 689 bp fragment with an EcoRI end preceding the ATG initiation codon, the entire coding sequence of mature IFN-γ, and 210 bp of noncoding sequence. The BglI end was then converted to an EcoRI end by ligation to a 29 bp Bgl I-ECoRI adaptor derived from the pre-IFN-γ EcoRI fragment described previously. Subsequent digestion of the ligation mixture with EcoRI would then generate a 718 bp EcoRI fragment containing the mature IFN-γ gene.

Figure 7:
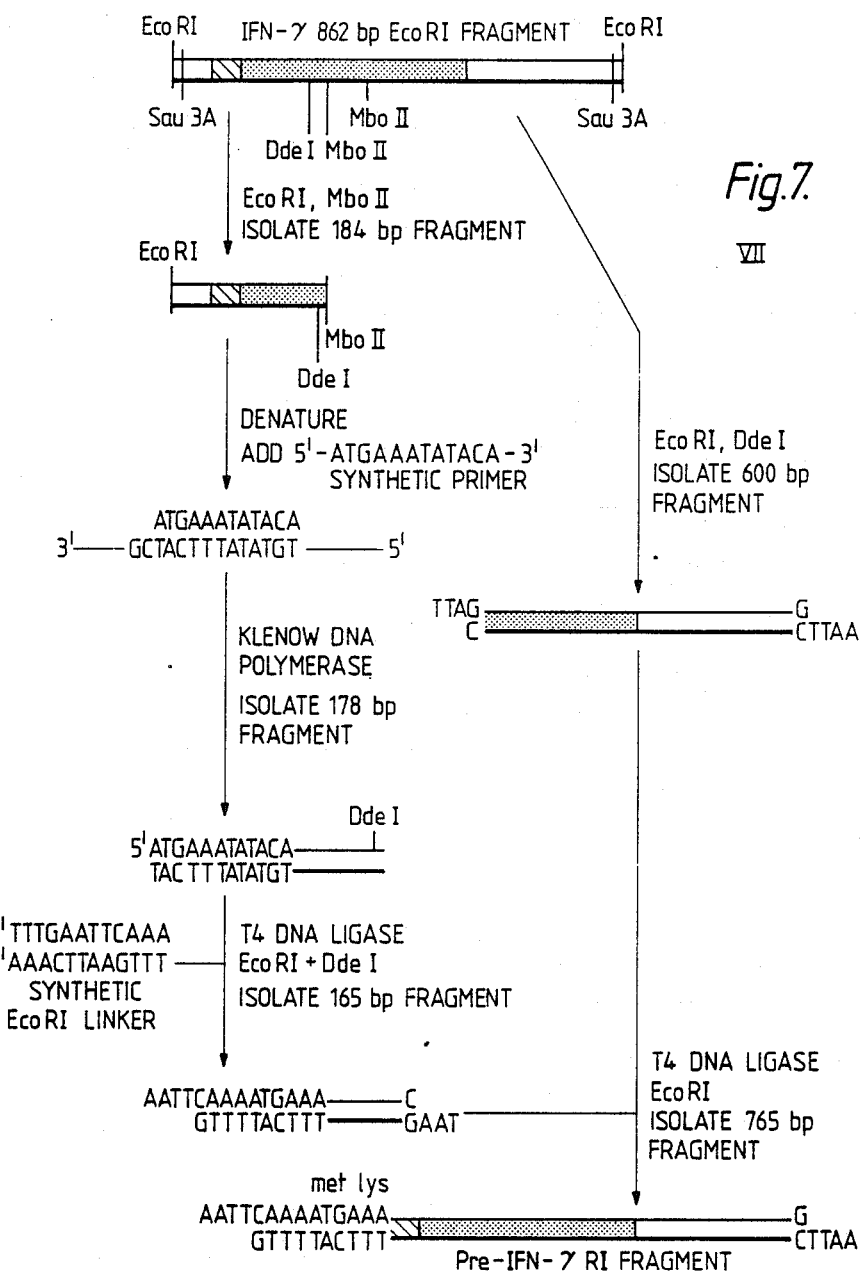
FIG. 7 shows the construction of an EcoRI fragment containing the pre-plus IFN-γ gene for the direct expression of IFN-γ in yeast.

FIG. 7 shows the construction of an EcoRI fragment containing the pre-IFN-γ gene with an EcoRI end and the sequence AAA preceding the ATG initiation codon. The EcoRI fragment containing the pre-IFN-γ gene described previously was digested with EcoRI and MboII to generate a 184 bp fragment. This fragment, containing the front part of the pre-IFN-γ gene, was heat denatured and annealed (10) to a 5'-kinased synthetic oligonucleotide 5'-pATGAAATATACA coding for the first four amino acids of the pre-IFN-γ gene. With the bottom strand of the EcoRI-MboII fragment, the template, and the oligonucleotide as the primer, Klenow fragment of *E. coli* DNA polymerase was used to synthesize the top strand and to remove the 3'-protruding end from the bottom strand. The resulting 178 bp blunt-ended fragment, which extends from the ATG initiation codon to first MboII site downstream, was then ligated to a self-complementary 5'-TTTGAATTCAAA-3' EcoRI linker. Digestion of the ligation mixture with EcoRI and DdeI generates a 165 bp EcoRI-DdeI fragment which contains the front part of the pre-IFN-γ gene. The entire gene was then assembled by ligating the 600 bp DdeI-EcoRI fragment that contains the back portion of the IFN-γ gene and the 3'-noncoding region. The ligation was then digested with EcoRI to generate a 765 bp EcoRI fragment containing the entire pre-IFN-γ gene.

Figure 8:
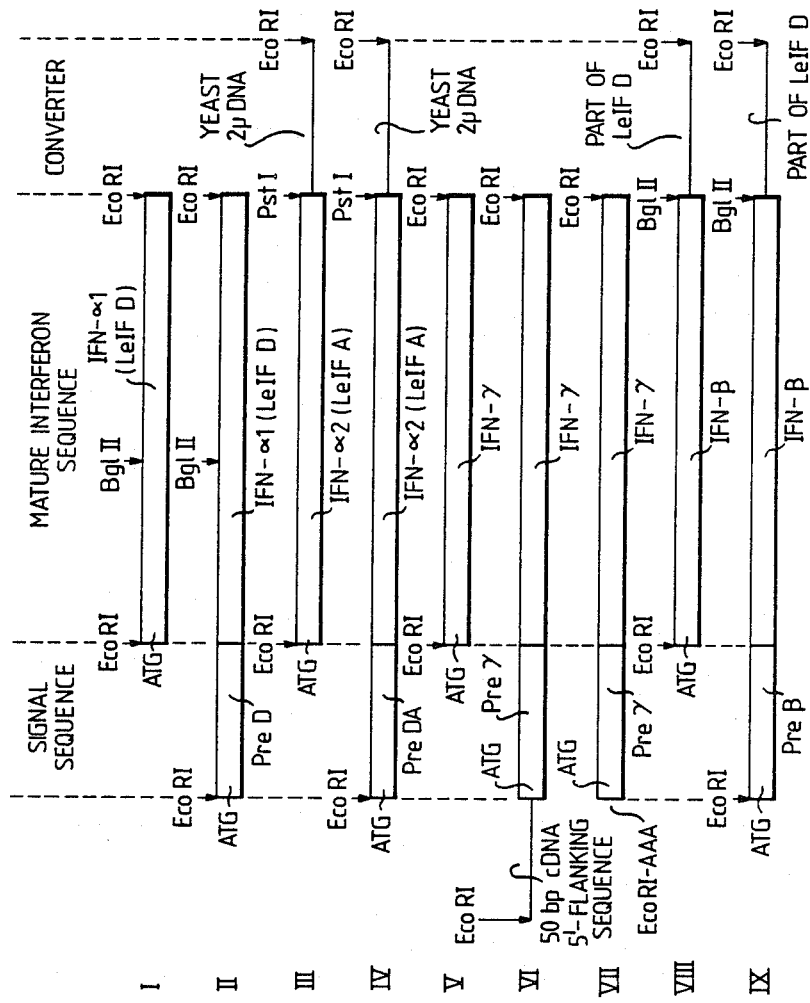
FIG. 8 provides a summary of all the constructs used to practice the present invention in the expression, processing and secretion of the various IFN genes in yeast.

A summary of all these EcoRI fragment constructions (I thru IX) is shown in FIG. 8. All these constructions were placed in the vector YEpIPT (FIG. 2) for expression and secretion experiments using yeast.

Expression and secretion levels of interferons by yeast containing these plasmids After the EcoRI-fragment genes from FIG. 8 were put into YEpIPT (FIG. 2), checked for orientation, and put into yeast, using Trp+ complementation, the yeast containing those plasmids were assayed for interferon using the cytopathic effect (CPE) assay (26) (bioassay) for extracts, released cell wall material, and media. Interferon assays were done on three distinct compartmental locations in the yeast culture. The results of such assays are shown in Table 1.

| Gene Construction No. | YEpIPT plasmid containing these EcoRI fragments | Yeast | Inside[a] cell U/l/Abs$_{660}$ = 1 | Pct.[b] cell protein | Released after cell wall removal[c] (U/l/Abs$_{660}$) | Pct. cell protein | Outside cell (media) U/l/Abs$_{660}$ | Pct. cell protein | Final[d] Abs$_{660}$ | Pct. of activity secreted[e] |
|---|---|---|---|---|---|---|---|---|---|---|
| I | LeIF D | GM3C-2 | $130 \times 10^6$ | 1.0 | 0 | 0 | 0 | 0 | 1.0 | 0 |
| II | pre LeIF D | GM3C-2 | $27 \times 10^6$ | 0.3 | $0.4 \times 10^6$ | .004 | $0.8 \times 10^6$ | .008 | 1.4 | 4 |
| III | LeIF A | pep4-3 | $130 \times 10^6$ | 1.0 | 0 | 0 | 0 | 0 | 1.0 | 0 |
| IV | (pre D/A) LeIF A | pep4-3 | $19 \times 10^6$ | 0.2 | $0.5 \times 10^6$ | .005 | $0.5 \times 10^6$ | .005 | 1.0 | 6 |
| IV | (pre D/A) LeIF A | pep4-3 | $25 \times 10^6$ | 0.3 | N.D. | — | $2 \times 10^6$ | .007 | 3–4 | 8 |
| IV | (pre D/A) LeIF A | GM3C-2 | $28 \times 10^6$ | 0.3 | $0.3 \times 10^6$ | .003 | $0.5 \times 10^6$ | .005 | 1.3 | 3 |
| V | IFN-γ | pep4-3 | $0.6 \times 10^6$ | N.D. | N.D. | — | 0 | 0 | 1.0 | 0 |
| VI | pre IFN-γ + cDNA 5' flanking sequence | pep4-3 | $0.2 \times 10^6$ | N.D. | N.D. | — | $.03 \times 10^6$ | N.D. | 1.2 | 15 |
| VI | pre IFN-γ + cDNA 5' flanking sequence | GM3C-2 | $0.38 \times 10^6$ | N.D. | N.D. | — | $.06 \times 10^6$ | N.D. | 0.93 | 16 |
| VII | pre IFN-γ | pep4-3 | $0.9 \times 10^6$ | N.D. | N.D. | — | $.19 \times 10^6$ | N.D. | 1.0 | 17 |

-continued

| Gene Construction No. | YEp1PT plasmid containing these EcoRI fragments | Yeast | Inside[a] cell U/l/Abs$_{660}$ = 1 | Pct.[b] cell protein | Released after cell wall removal[c] (U/l/Abs$_{660}$) | Pct. cell protein | Outside cell (media) U/l/Abs$_{660}$ | Pct. cell protein | Final[d] Abs$_{660}$ | Pct. of activity secreted[e] |
|---|---|---|---|---|---|---|---|---|---|---|
| VII | pre IFN-γ | GM3C-2 | $1.9 \times 10^6$ | N.D. | N.D. | — | $.19 \times 10^6$ | N.D. | 0.93 | 10 |

[a] See Methods for extract preparation. Note that two methods are used for extracts. When cells are spheroplasted the "inside cell" amount is really inside material; however, when N.D. (not determined) is specified the "inside cell" amount and the "released after cell wall removal" are both part of "inside cell" amount-this type of extract involves glass beading cells without cell wall removal. Note that glass bead extracts without spheroplasting were always done for IFN-γ and pre IFN-γ and that PBS buffer was used instead of 7 M GHCl.
[b] The specific activities of LeIFA and LeIFD are both assumed to be $10^8$ U/mg protein for the calculations. A yeast culture contains about 100 mg of protein in the culture at an Abs$_{660}$ = 1.
[c] See Methods for spheroplasting procedure.
[d] Abs of culture at which assay done.
[e] The percent secretion is the percent "released after cell wall removal" plus the percent "outside cell". When spheroplasting was not done the "percent of activity secreted" does not include this cell wall secretion activity and the percent is lower (maybe ½) than it actually should be.

The first compartment is inside the cell. This fraction is measured by making a cell extract after the cell wall is removed and defines interferon activity that is not secreted. The other two compartments are the media (material completely separate from yeast cell) and the activity released from the cells after cell wall removal using zymolyase (secreted material but trapped non-covalently in cell wall). Both the media fraction and fraction released after cell wall removal represent the total secreted material. Alternatively when cell walls were not removed (see Methods), inside the cell activity also includes the secreted activity stuck in the cell wall.

It should be noted on Table 1 that (pre D/A) LeIFA is a mature LeIFA gene with a hybrid signal peptide sequence (see FIGS. 1 and 8). This construction has been previously discussed; but in review it was constructed by using the DdeI restriction site common to both preLeIFD and preLeIFA. FIG. 1 shows this DdeI site at amino acid −10. The underlined amino acids represent differences between the amino acid sequence of preLeIFD and preLeIFA. The hybrid (pre D/A) LeIFA is more like preD than preA.

Both mature LeIFA and LeIFD genes (constructions I and III) are expressed in the yeast at levels of 1.0 percent of the total cellular protein (levels of 2.0 percent have also been seen). The wrong orientations of these genes or the pre-genes do not express. For these two genes as well as the mature IFN-α gene, no secretion occurs. However, when presequences are used on these genes, all three protein products are found in the media as secreted products. Levels as high as 8 percent of the total activity have been observed in the media of (pre D/A) LeIFA at an Abs$_{660}$=3-4. It should be noted that all these plasmids are in 95 percent of the cells of a culture growing under Trp+ selective pressure attesting to the presence of an autonomous replicating plasmid.

Growth Curve and Production in the Media from a Yeast Containing the (pre D/A) LeIFA Gene Two interferon-producing yeast were investigated by further characterization. These were YEp1PT-preLeIFA53t/pep4-3 and YEp1PT-LeIFAI/pep4-3. The former contains two copies of construction IV (FIG. 8) in the EcoRI site of YEp1PT and results in activity being inside the cell, in the cell wall, and outside the cell (media). This two copy gene (in tandem - both in orientation for proper expression) containing plasmid was used instead of the single copy construction since it sometimes gave higher levels of interferon activity in the media. Pep 4-3 yeast was used since it has greatly reduced intracellular and extracellular protease levels (23), which might be an advantage for obtaining undegraded protein (interferon) from the media.

The latter contains construction III (FIG. 8) in YEp1PT and expresses mature LeIFA inside the cell but does not secrete.

Figure 9:
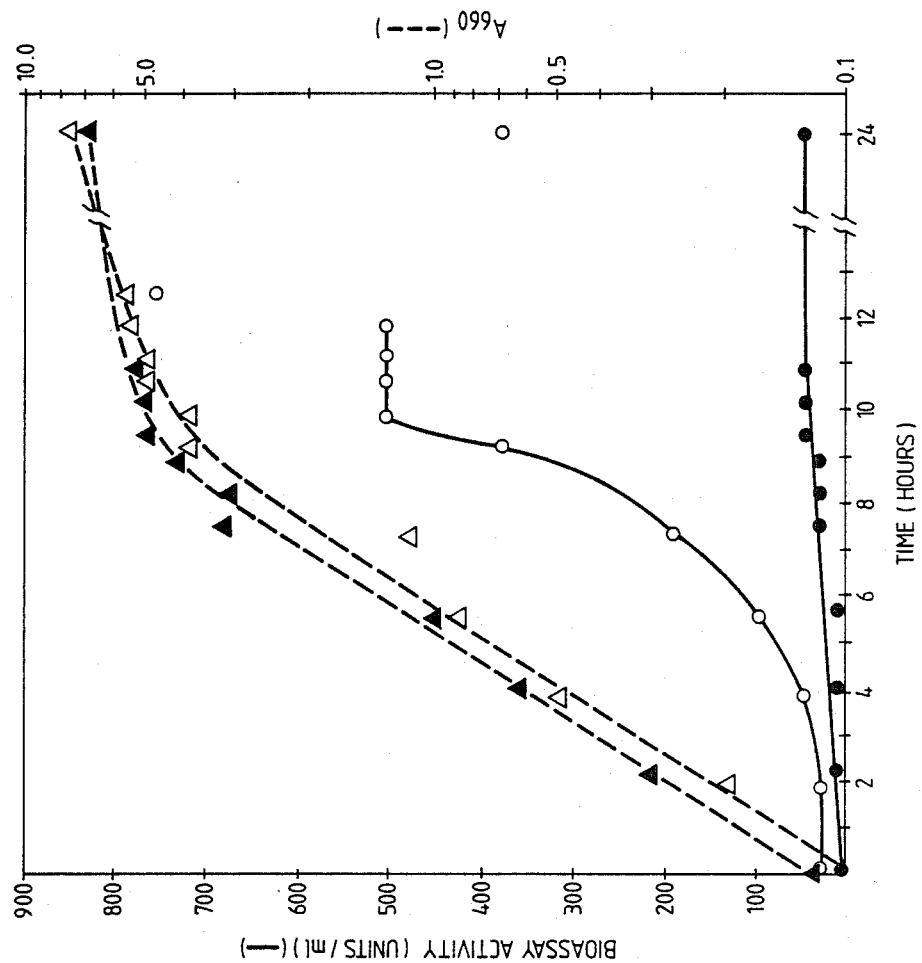
FIG. 9 is a growth curve of (a) YEp1PT-LeIFA1/pep4-3 and (b) YEp1PT-preLeIFA53t/pep4-3 measured by Abs$_{660}$ mμ. Media was assayed for interferon activity for (a) and for (b) using a bioassay. Time refers to hours of growth at 30° C.

FIG. 9 illustrates a growth curve of these two yeast strains in YNB+CAA (Trp+ selective growth). Log phase continues to an Abs660mμ of 3-4 and then stationary phase begins. Both curves are essentially identical (suggesting that the production of these two different proteins [LeIFA and (preD/A) LeIFA] does not affect yeast growth or viability. Bioassays were done on the media at various times during cell growth, to investigate the growth curve dependence of production of interferon in the media by these two strains. It is evident from these results that the pre-sequence on LeIFA is causing a release of interferon activity into the media. Without this sequence essentially no activity is released. It is also evident that levels of activity in the media reach a maximum near stationary phase.

Purification of (pre D/A) LeIFA from the media

In order to determine the nature of the secretion process for (pre D/A) LeIFA into yeast media, it was necessary to purify the protein product from the media. If yeast is able to secrete the protein, it probably processes the amino-terminal end in some manner during the secretion process as mammalian cells normally do with a pre-interferon protein. The object of further experiments was to determine the nature of this processing, as follows:

(A) 5 l Fermentation

Figure 10A:
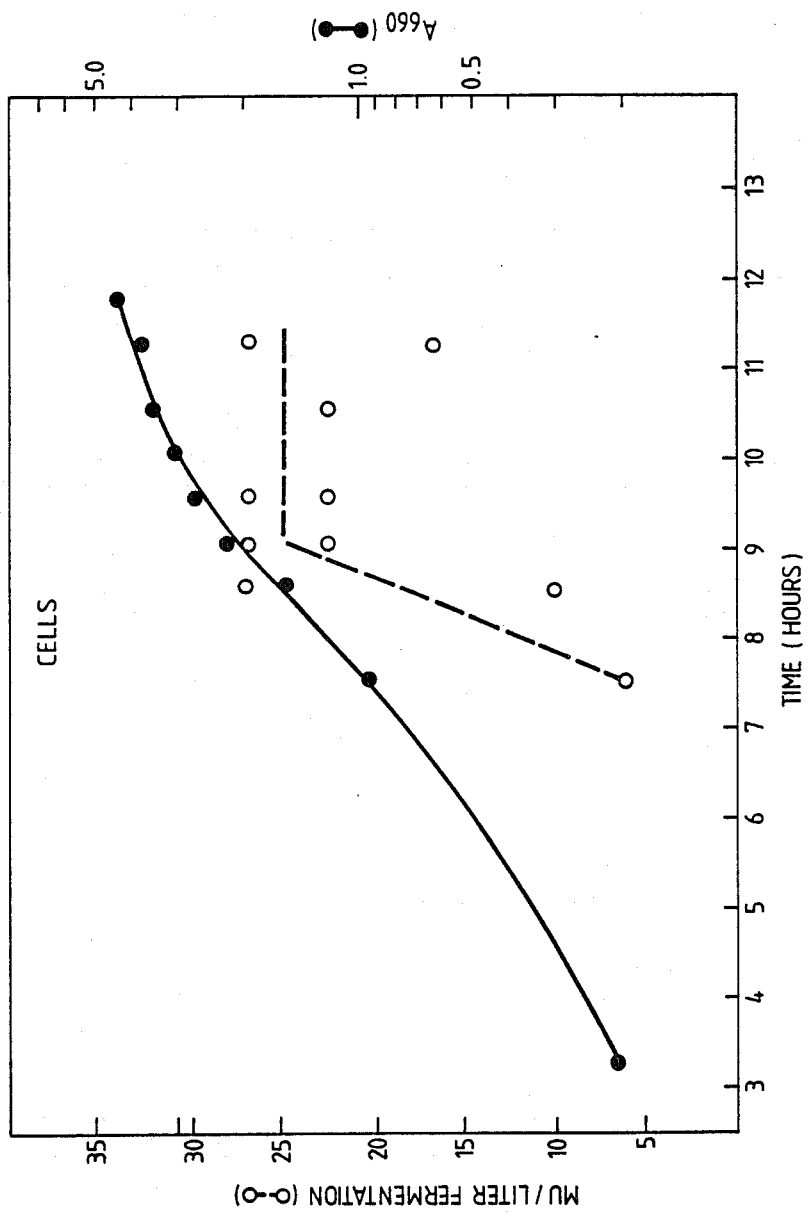
FIG. 10A is a growth curve for a 5 l fermentation of YEp1PT-preLeIFA53t/pep4-3. (θ) is ABs$_{660}$ mμ and (O) million units per liter of interferon activity inside the cells.

FIG. 10A shows the interferon activity within the cell wall and in the cell during the same fermentation. These extracts were done by pelleting followed by glass bead treatment in 7M GHCl so this activity contains both intracellular and intracell-wall material. This activity reached a maximum of about $25 \times 10^6$ U/l at an Abs$_{660}$mμ of 1.5 to 2.0, suggesting that intracellular interferon production ends in log phase before stationary unlike extracellular material. Thus about 8 percent of the activity is secreted freely into the media. However, again as much activity may be in the cell wall (see Table 1). The extract material contains mostly intracellular interferon and this material is presently being purified to see if it is processed or unprocessed.

Figure 10B:
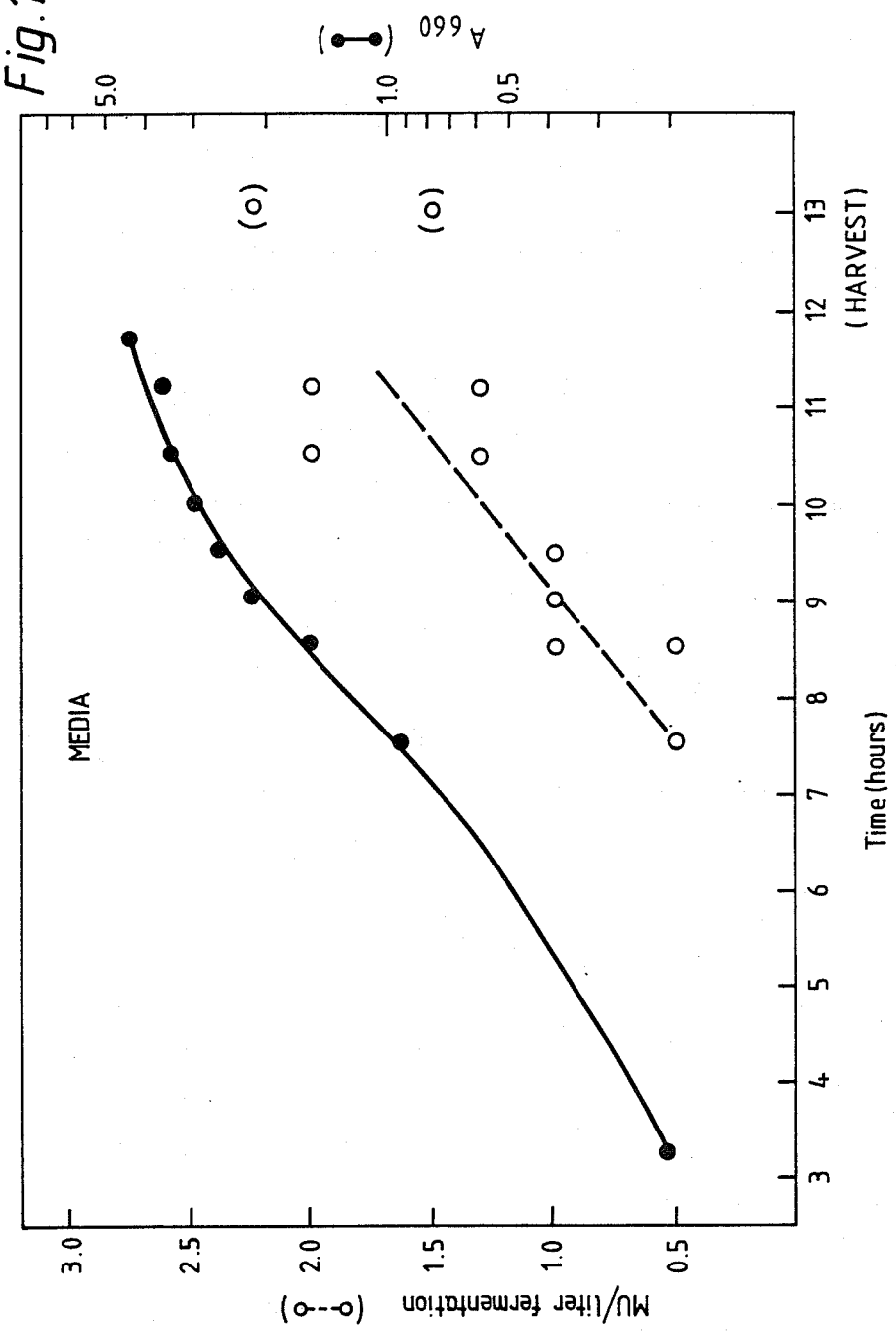
FIG. 10B is the same growth curve as defined in FIG. 10A graphing activity from the media.

FIG. 10B shows a growth curve for a 5 l fermentation of YEp1PT-preLeIFA 53t/pep4-3 in YNB+CAA. At the end of the fermentation there were about $2.0 \times 10^6$ U/l of interferon activity by MDBK assays. Again the maximum production is seen at stationary phase. It should be noted that the interferon product in this medium is very stable even with 24h of additional shaking at 30° C. after stationary phase is reached. This medium was used for further purification steps.

(B) Media Concentrate onto Immunoaffinity Column

The medium from YEp1PT-preLeIFA53t/pep4-3 was first ultrafiltered. This concentrate was put on a column containing a monoclonal antibody to mature LeIFA. After washing with 0.2 MNaCl in tris/cys-/EDTA, pH=8.0, the interferon was eluted with $H_2O$ (pH=5.5) as shown in FIG. 11. Eluted peak A (arrow represents when $H_2O$ applied) was obtained by this procedure and represents 50 percent of the activity put on the column. Peak A was pooled, as shown by bracket and used for further purification. Elution with 0.2M acetic acid resulted in peak B (arrow represents point of buffer change) and position C represents point of application of original wash buffer.

(C) HPLC Run of Peak A Activity

Peak A fractions were lyophilized to dryness and then run on HPLC (see Methods). FIG. 12 illustrates the results of this run. A 2.5 μg sample of purified LeIFA (from *E. coli*) was run separately as a control.

Both the standard and (pre D/A) LeIF A (or pre-LeIF A) had identical retention times as is evident in the figure. These results show that the interferon from the media is processed, since preLeIF A has a much different retention time. The shaded fraction from this HPLC run was then used for protein sequence.

NH$_2$-terminal sequence of (pre D/A) LeIF A Purified from Yeast Media

Figure 13:
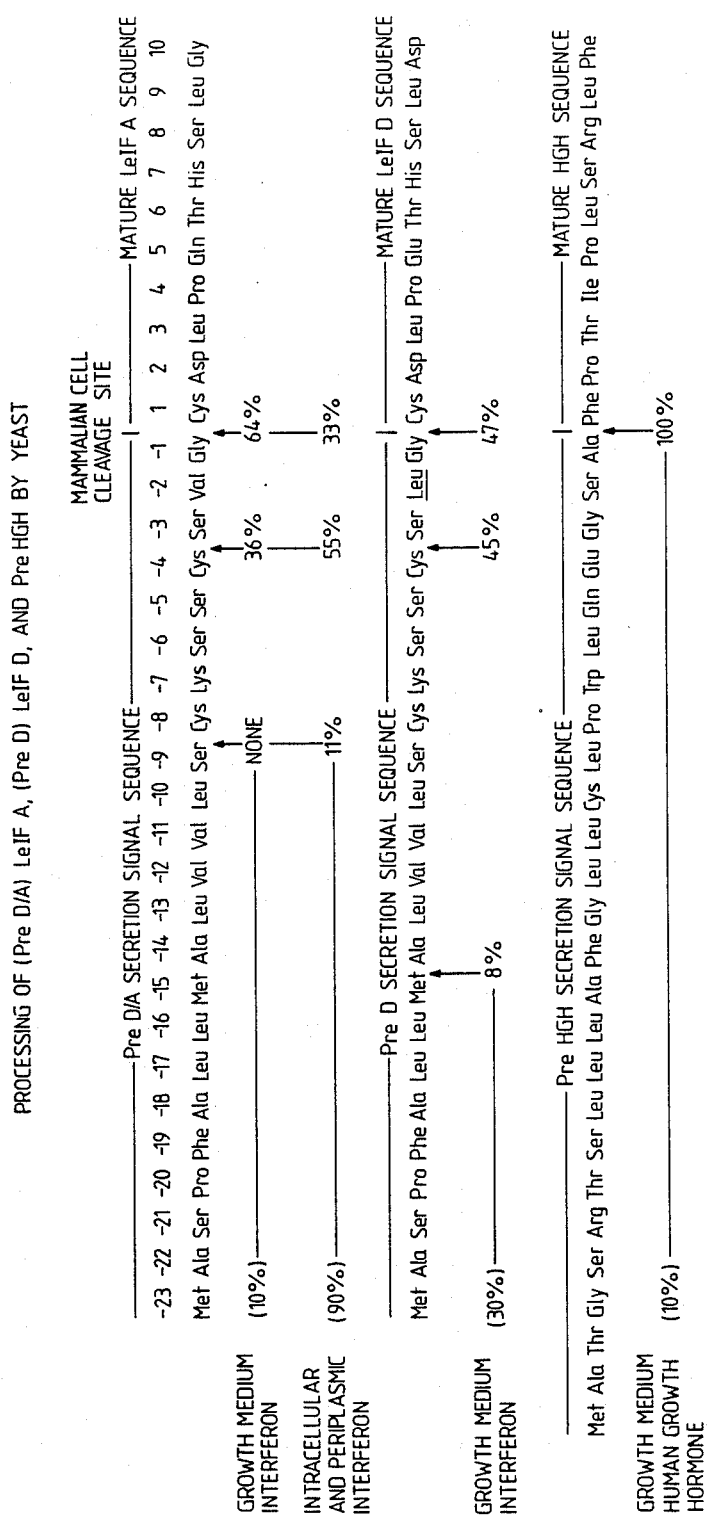
FIG. 13 is the result of amino acid sequencing of product obtained after HPLC purification.

FIG. 13 in part shows the results of sequencing the purified interferon. The upper sequence is that expected for (pre D/A) LeIF A if no processing occurs. The normal cleavage point of this interferon that is probably recognized by mammalian cells is shown.

The protein sequence was interpreted by noting which PTH amino acid increased in each corresponding Edman cycle and then decreased in the following cycle. PTH amino acid that normally give low recoveries (cys, ser, thr, arg, his) were assumed when no increase in any other PTH amino acid was seen. The mg amount was estimated by comparing the areas of the interpreted residue with the area from a standard mixture of PTH amino acids run on the same HPLC. An internal standard of Nor-Leucine was introduced in each chromatogram to assure that retention times were reproducible.

FIG. 13 shows the protein sequencing results obtained for the purified (pre D/A) LeIF A. The sequence expected if no processing were to occur and the normal cleavage point of this pre-interferon in mammalian cells are also shown. Two independent sequence runs were performed on two different purified samples from cells and media. FIG. 13 shows that most of the interferon in the medium was properly processed (64 percent), but another form (36 percent) containing three additional amino acids of pre-sequence was also present. The intracellular interferon also contained these two forms, but in slightly different proportions, as well as a third form containing 8 amino acids of pre-sequence. Full length pre-sequence was never observed, suggesting that yeast processes all of the pre-IFN in some manner.

It is possible that the processed form containing three amino acids of pre-sequence resulted from the hybrid nature of the pre D/A signal sequence. Therefore, the processing of the non-hybrid (pre D) LeIF D was also examined. Pre D is different from pre D/A only at amino acid position -2 (leu versus val). When the processing of pre IFN-α1 purified from the medium was examined, both the +1 and −3 forms were again observed (FIG. 13). However, a minor species was also present in the medium as a −14 form, which was not seen for (pre D/A) LeIF A.

To investigate the secretion of heterologous proteins from *S. cerevisiae*, we have constructed plasmids for *in vivo* transcription of the genes for several mature interferons (IFNs) and several pre IFNs. Whenever the coding sequences for hydrophobic signal peptides were present, IFN antiviral activity could be recovered both from the host cells and from the culture medium, while all of the IFN whose synthesis was directed by mature IFN genes remained inside the cells. We have attempted to characterize the requirements for secretion by undertaking constructions in which the interferon gene would be provided with its own natural signal sequences, as in (pre D) LeIF D, or would be provided with a hybrid signal sequence designed as a composite of two IFN-α species, as in (pre D/A) LeIF A. While, in general, the yeast cells which harbored these constructions secreted IFN into the culture medium, the amount of activity differed between strains, and the IFN species purified and sequenced also differed.

Three forms of non-secreted interferon, constituting 90 percent of the total interferon expressed, were purified from cells harboring the (pre D/A) LeIF A gene. One form (33 percent) was properly processed (+1, FIG. 13), a second form (55 percent) contained 3 additional amino acids (−3, FIG. 13), and a third form (11 percent) contained 8 additional amino acids (−8). The last form was not seen in medium, while IFN with a full length pre-sequence was never observed in the cells or media.

Processing of (pre D) LeIF D

Instead of the shake flask growth used for (pre D/A) LeIF A yeast, (pre D) LeIF D expressing yeast were grown in a 10 liter fermenter to an $A_{550}=60$.

When the processing of (pre D) LeIF D purified from the medium (purification same as for pre D/A LeIF A) was examined, both the +1 and −3 forms were observed (FIG. 13). An additional, minor species was also present in the medium as a −14 form. There was no evidence of cell lysis occurring in the culture as examined by SDS gel electrophoresis of medium protein versus cellular proteins. Interestingly, at this high growth density, a very high percentage secretion (30 percent) into the medium was obtained for LeIF D. High density fermentations of (pre D/A) LeIF A expressing yeast also show this higher percentage secretion.

Yeast appear to process both the secreted and nonsecreted interferon. The amount of activity secreted varies depending on the growth stage of the cells, with maximum percentages occurring at stationary phase in shake flasks and at the end of high density fermentations (30 percent in media).

Confirmation of the Composition of the plasmids in YEp1PT-preLeIFA53t and YEp1PT-LeIFA1 Containing Yeast The yeast containing these two plasmids and used for the previous experiments were further checked by retrieval of the plasmids from the yeast. This was done by isolation of the plasmid DNA from yeast extract by transformation of E. coli, followed by miniscreen DNA preparation and restriction analysis of the plasmid DNAs. Several E. coli isolated plasmid DNAs were characterized for both types of yeast. In all cases the plasmids contained the restriction sequence expected, attesting to the presence of the presequence on (pre D/A) LeIF A containing plasmid and the lack of it on mature LeIF A containing plasmid.

Restriction Map and Partial Sequencing of 3.1 kb Insert of pB1

Figure 15:
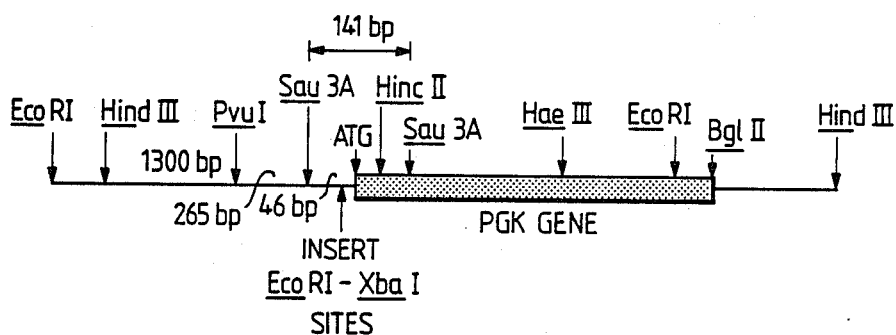
FIG. 15 schematically illustrates the restriction map of the 3.1 kbp HindIII insert of vector pBI from which the PGK promoter was isolated. Indicated is the insertion of an EcoRI site and an XbaI site in the 5'-flanking DNA of the PGK gene.

300 μg of pB1 (37a) was exhaustively digested with HindIII in a 500μl reaction volume, then electrophoresed on a 1 percent agarose preparative agarose (Sea Kem) gel. The 3.1 kb HindIII insert was cut from the ethidium stained gel, electroeluted (39), 2x extracted with equal volumes of buffer-saturated phenol and chloroform before ethanol precipitation. Portions of the resuspended DNA fragment were divided up and subjected to restriction cuts with a group of different restriction enzymes to yield the partial restriction map depicted in FIG. 15.

30 μg of the purified 3.1 kb insert was cut with Sau3A then run on a 6 percent acrylamide gel. Fragments corresponding to the 265 bp and 141 bp were separately purified by electroelution as described above. Each DNA fragment was then subjected to DNA sequence analysis (39).

A portion of this DNA sequence is shown in FIG. 16. Amino acids corresponding to the N-terminal amino acids of the PGK structural gene are printed above the DNA sequence.

Insertion of a Restriction Site in the PGK 5' Promoter Region

A synthetic oligonucleotide with the sequence 5'ATTTGTTGTAAA3' was synthesized by standard methods (40). 100 ng of this primer was labeled at the 5' end using 10 units of T4 polynucleotide kinase in a 20 μl reaction also containing 200 μCi of [γ$^{32}$-P] ATP. This labeled primer solution was used in a primer-repair reaction designed to be the first step in a multi-step process to put an EcoRI restriction site in the PGK 5'-flanking DNA just preceeding PGK structure gene sequence. The multistep process is explained below:

Step 1

(FIG. 17)

Primer repair reactions and cloning of 39bp XbaI-to-Sau3A PGK piece

100 μg of pBI was completely digested with HaeIII, then run on a 6 percent polyacrylamide gel. The uppermost band on the ethidium stained gel (containing PGK promoter region) was isolated by electroelution as described above. This 1200 bp HaeIII piece of DNA was restricted with HindII then run on a 6 percent acrylamide gel. The 650 bp band was isolated by electroelution. 5 μg of DNA was isolated. This 650 bp HaeIII-to-HindII piece of DNA was resuspended in 20 μl dIH$_2$O, then mixed with the 20 μl of the phosphorylated primer solution described above. This mixture was 1X phenol-chloroform extracted, then ethanol precipitated. Dried DNA was resuspended in 50 μl of H$_2$O and then heated in a boiling water bath for seven minutes. This solution was then quickly chilled in a dry ice-ethanol bath (10-20 seconds), then transferred to an ice-water bath.

Figure 17:
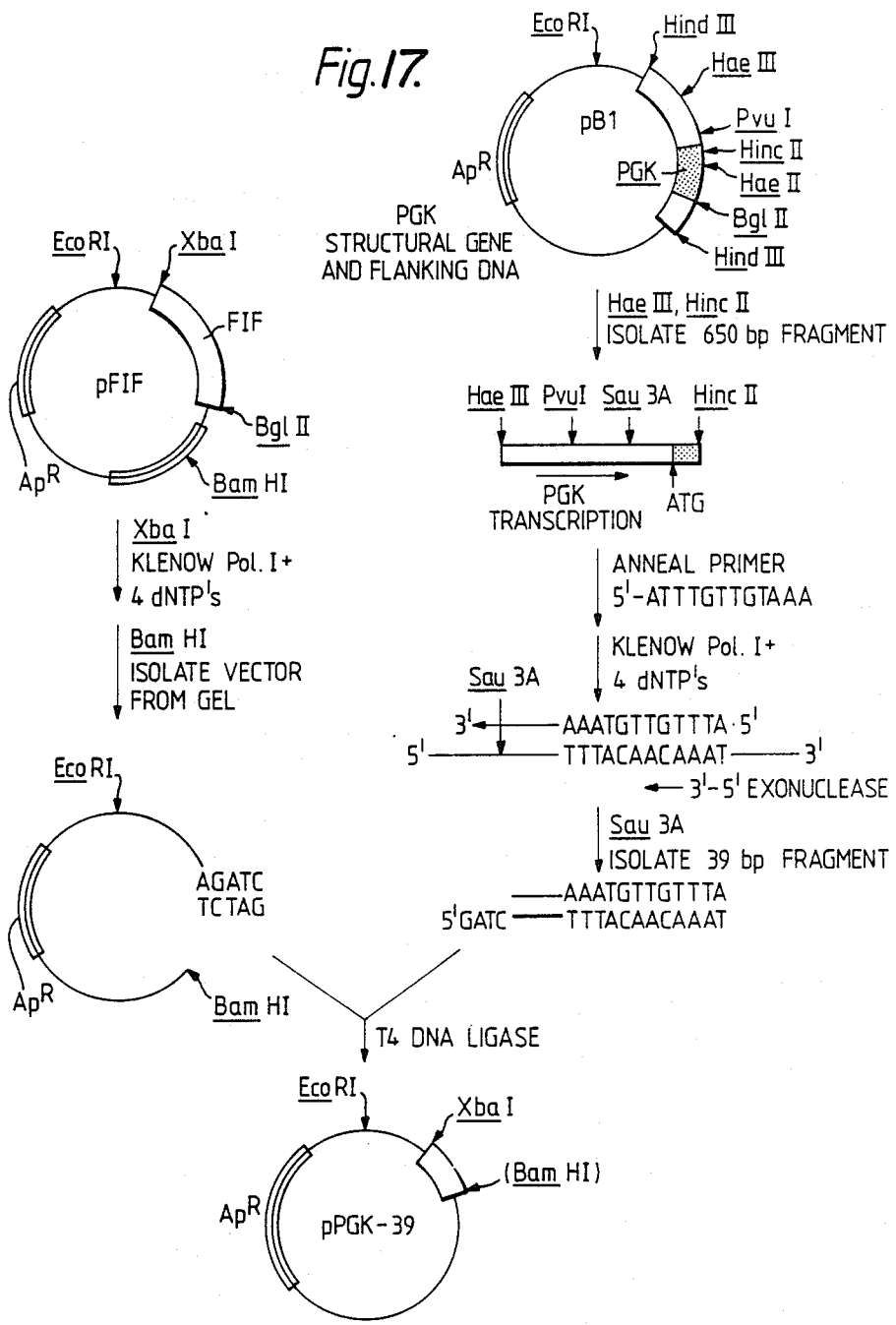
FIG. 17 schematically illustrates techniques used to insert an XbaI site at position - 8 in the PGK promoter and to isolate a 39 bp fragment of the 5'-flanking sequence of PGK containing this XbaI end and a Sau3A end.
Figure 18:
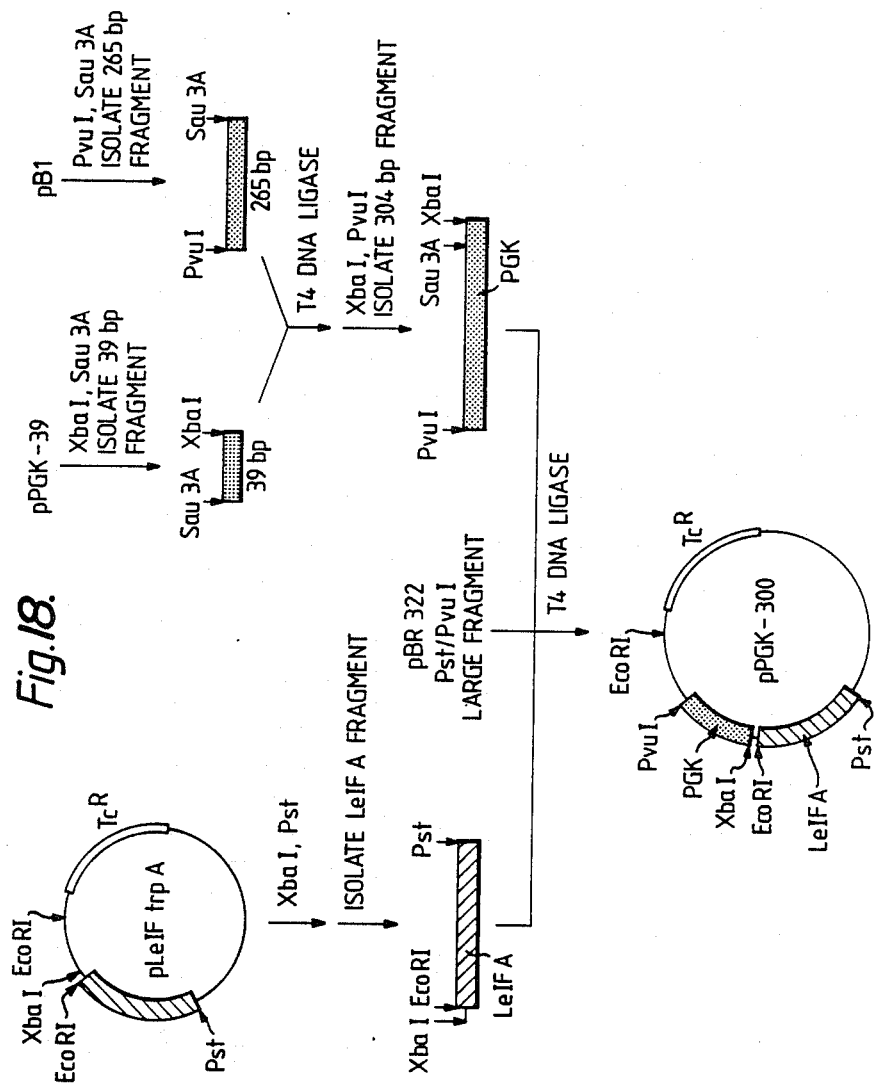
FIG. 18 schematically illustrates the construction of a 300 bp fragment containing the above 39 bp fragment, additional PGK 5'-flanking sequence (265 bp) from PvuI to Sau3A (see FIG. 15), and a EcoRI site adjacent to XbaI.
Figure 19:
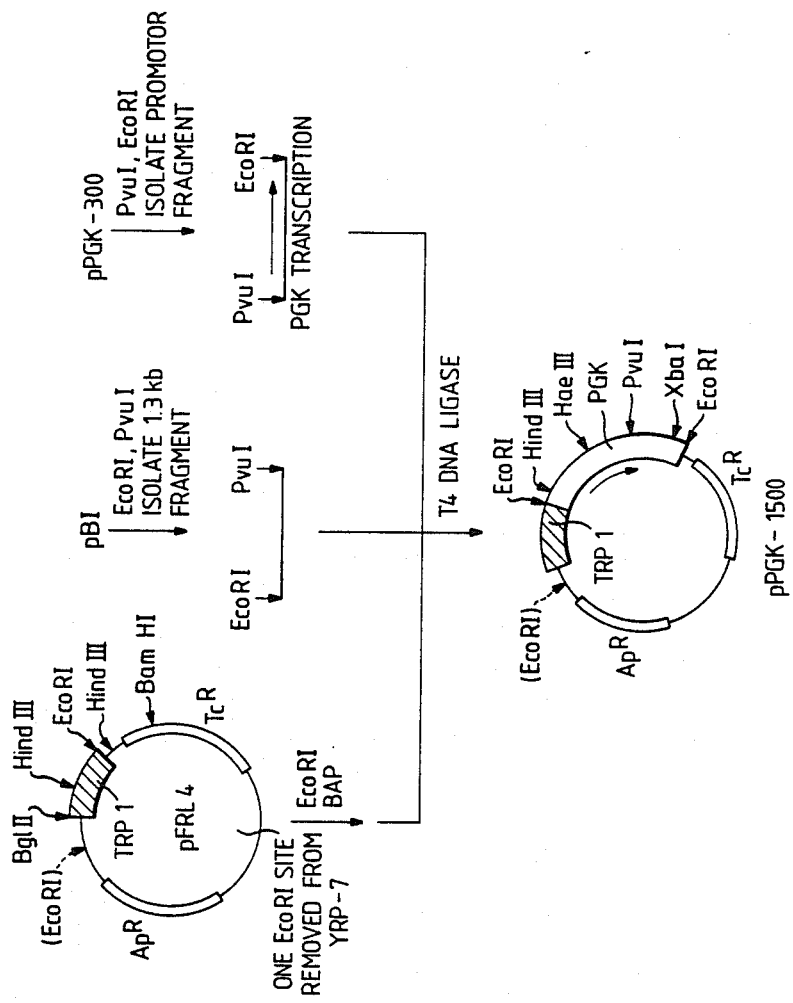
FIG. 19 schematically illustrates the construction of the 1500 bp PGK promoter fragment (HindIII/EcoRI) which contains, in addition to the fragment constructed in FIG. 4, a 1300 bp HindIII to PvuI fragment from PGK 5'-flanking sequence (see FIG. 15).

To this solution was added 50 μl of a solution containing 10 μl of 10X DNA polymerase I buffer (Boehringer Mannheim), 10 μl of a solution previously made 2.5 mM in each deoxynucleoside triphosphate (dATP, dTTP, dGTP and dCTP), 25 μl of dIH$_2$O and 5 units of DNA Polymerase I, Klenow fragment. This 100 μl reaction was incubated at 37° C. for 4 hours. The solution was then 1X phenol-chloroform extracted, ethanol precipitated, dried by lyophilization, then exhaustively restricted with 10 units of Sau3A. This solution was then run on a 6 percent acrylamide gel. The band corresponding to 39 bp in size was cut from the gel, then isolated by electroelution described above. This 39 bp band has one blunt end and one Sau3A sticky end. This fragment was cloned into a modified pFIFtrp69 vector (10). 10 μg of pFIFtrp69 was linearized with XbaI, 1X phenol chloroform extracted, then ethanol precipitated. The XbaI sticky end was filled in using DNA Polymerase I Klenow fragment in a 50 μl reaction containing 250 μM in each nucleoside triphosphate. This DNA was cut with BamHI, then run on a 6 percent acrylamide gel. The vector fragment was isolated from the gel by electroelution then resuspended in 20 μl dIH$_2$O. 20 ng of this vector was ligated with 20 ng of the 39 bp fragment synthesized above for 4 hours at room temperature. One-fifth of the ligation mix was used to transform E. coli strain 294 to ampicillin resistance (on LB +20 μg/ml amp plates). Plasmids from the transformants were examined by a quick screen procedure (20). One plasmid, pPGK-39 (FIG. 17), was selected for sequence analysis. 20 μg of this plasmid was digested with XbaI, ethanol precipitated, then treated with 1000 units of bacterial alkaline phosphatase at 68° C. for 45 min. The DNA was 3X phenol-chloroform extracted, then ethanol precipitated. The dephosphorylated ends were then labeled in a 20 μl reaction containing 200 μCi of [δ$^{32}$-P] ATP and 10 units of T$_4$ polynucleotide kinase. The plasmid was cut with SalI and run on a 6 percent acrylamide gel.

The labeled insert band was isolated from the gel and sequenced by the chemical degradation method (39). The DNA sequence at the 3'-end of this promoter piece was as expected.

Step 2

(FIG. 18)

Construction of 312 bp PvuI-to-EcoRI PGK Promoter Fragment

25 μg of pPGK-39 (FIG. 17) was simultaneously digested with SalI and XbaI (5 units each), then electrophoresed on a 6 percent gel. The 390 bp band containing the 39 bp promoter piece was isolated by electroelution. The resuspended DNA was restricted with Sau3A, then electrophoresed on an 8 percent acrylamide gel. The 39 bp PGK promoter band was isolated by electroelution. This DNA contained 39 bp of the 5' end of the PGK promoter on a Sau3A-to-XbaI fragment.

25 μg of pB1 was restricted with PvuI and KpnI, then electrophoresed on a 6 percent gel. The 0.8 kbp band of DNA was isolated by electroelution, then restricted with Sau3A and electrophoresis on a 6 percent gel. The 265 bp band from the PGK promoter (FIG. 15) was isolated by electroelution.

This DNA was then ligated with the 39 bp promoter fragment from above for two hours at room temperature. The ligation mix was restricted with XbaI and PvuI, then electrophoresed on a 6 percent acrylamide gel. The 312 bp Xba-to-PvuI restriction fragment was isolated by electroelution, then added to a ligation mix containing 200 ng of pBR322(33) [previously isolated missing the 162 PvuI-to-PstI restriction fragment] and 200 ng of the XbaI-to-pst I LeIFA cDNA gene previously isolated from 20 µg of pLEIFtrpA. This 3-factor-ligation mix was used to transform E. coli strain 294 to tetracycline resistance. Transformant colonies were miniscreened and one of the colonies, pPGK-300, was isolated as having 304 bp of PGK 5'-flanking DNA fused to the LeIFA gene in a pBR322 based vector. The 5' end of the LeIFA gene has the following sequence: 5'-CTAGAAATTC-3'; thus fusion of the XbaI site from the PGK promoter fragment into this sequence allows for the addition to the XbaI site an EcoRI site. pPGK-300 thus contains part of the PGK promoter isolated in a PvuI-to-EcoRI fragment.

Step 4

(FIG. 19)

Construction of a 1500 bp EcoRI-to-EcoRI PGK Promoter Fragment

10 µg of pBI was digested with PvuI and EcoRI and run on a 6 percent acrylamide gel. The 1.3 kb PvuI-to-EcoRI DNA band from the PGK 5'-flanking DNA was isolated by electroelution. 10 µg of pPGK-300 was digested with EcoRI and PvuI and the 312 bp promoter fragment was isolated by electroelution after electrophoresing the digestion mix on a 6 percent gel. 5 µg of pFRL4 was cut with EcoRI, ethanol precipitated, then treated with bacterial alkaline phosphatase at 68⁻ for 45 minutes. After 3X phenol/chloroform treating the DNA, ethanol precipitation, and resuspension in 20 ml of dIH$_2$O; 200 ng of the vector was ligated with 100 ng of 312 bp EcoRI-to-PvuI DNA from pPGK-300 and 100 ng of EcoRI-to-PvuI DNA from pBI. The ligation mix was used to transform E. coli strain 294 to ampicillin resistance. From one of the Ap$^R$ colonies was obtained pPGK-1500. This plasmid contains the 1500 bp PGK promoter fragment as an EcoRI-to-EcoRI or HindIII-to-EcoRI piece of DNA.

Figure 14:
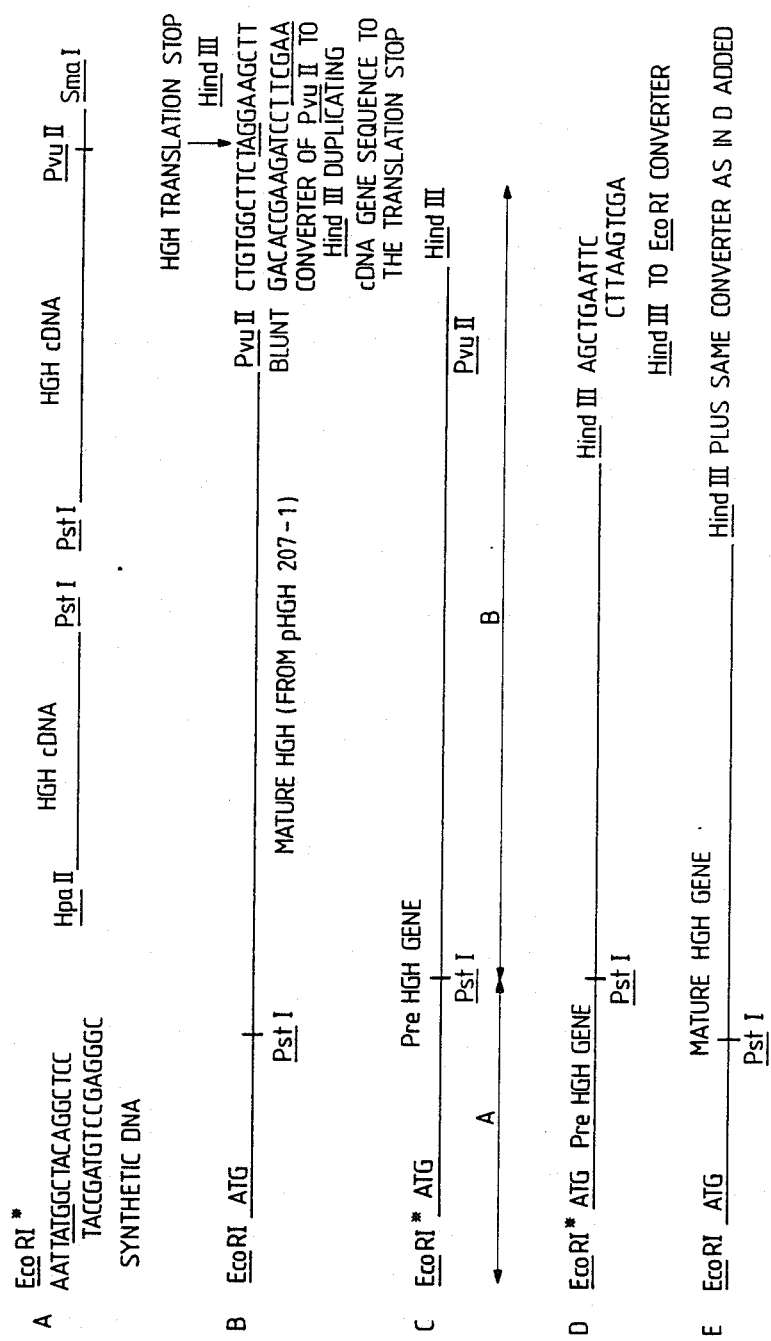
FIG. 14 depicts the various constructions employed to produce human growth hormone (HGH) in accordance herewith.

Construction of mature HGH (human growth hormone) and preHGH expression plasmids Constructions A through E of FIG. 14 were constructed in vectors with convenient sites. In construction A, a synthetic DNA was made to duplicate the DNA sequence at the beginning of the preHGH cDNA (42) from the Hpa II site with the formation of an EcoRI in front of the ATG translational start. The HpaII to PstI fragment was obtained from the preHGH cDNA (42) and this fragment with the synthetic DNA was ligated with an EcoRI to PstI vector (pHGH 207-1, with EcoRI to Pst1 fragment containing part of Ap$^R$ gene removed and both sites religated after Klenow fill in to remove both sites) containing from the PstI to SmaI site of the HGH cDNA (43) to obtain Construction A. Construction B was made from a plasmid containing the mature HGH gene which has previously been hooked up for direct expression containing 23 amino acids of synthetic coding sequence at the NH$_2$-terminal end (44). A plasmid containing this gene was cut with PvuII in the HGH gene and BamHI in the Tc$^R$ gene. The large fragment containing most of the gene was then ligated with synthetic DNA that duplicates the end of the HGH gene (TAG) and creates a HindIII site. This HindIII site was ligated with the HindIII/BamHI fragment of pBR322 as the 3rd factor of a 3 factor ligation to obtain a plasmid containing Construction B. Construction B therefore contained DNA encoding preHGH which was free of the normal 5' cDNA flanking sequences.

A and B were then combined as shown in FIG. 14 to give Construction C. C was further modified to give D, where the HindIII site was converted to an EcoRI (or EcoRI) site. The EcoRI piece thus obtained was placed in the EcoRI site of the yeast expression plasmid YEpIPT for expression of the preHGH gene in yeast. Construction E was also made using the converter used in D to obtain a mature interferon gene (without the secretion signal sequence) on an EcoRI fragment for expression in YEpIPT.

Expression of mature HGH and preHGH in Yeast

The mHGH Construction (E) in YEpIPT was placed into strain pep4-3 trp1 (20B-12) and extracts were prepared using glass beads as described in methods. However, glass beads were added to 10 ml of pelleted cells with 0.5 ml of 0.1 percent SDS. Dilutions were made in horse serum and RIA assays were done as previously described (44).

By RIA, HGH was expressed as about 0.5 percent of total yeast protein at an A$_{660}$ of 1.0 (0.5 mg/1/A$_{660}$). No HGH was detected in the medium.

The preHGH Construction (D) in YEpIPT was also put into yeast and cells and medium were assayed for HGH. A lower level of expression was detected in the cell (0.08 mg/1/A$_{660}$) or about 0.08 percent of total yeast protein. Thus, the level is about 1/6 of that of mature HGH expression, which is very similar to the leukocyte interferon results. However, this may not be a fair comparison since the codon usage of mature HGH (44) is different for 23 amino acids than the same amino acids for the preHGH. Such a difference may result in differences in the level of expression of these two products (45). Ten percent or 8 ug/1/(A$_{660}$=1) of the level expressed in the cell was found in the medium of the preHGH expressing yeast. In a 10 l fermentor at an A$_{550}$=85, again there was about 10 percent secretion with 1 mg/l HGH in the media.

The Nature of PreHGH Expression

A comparison of HGH protein in the cell versus that outside the cell was made using a Western blotting procedure as described above. The results show medium from a high density fermentation (A$_{550}$=85) of preHGH expressing yeast. A single band corresponding to mature HGH size is present. This band corresponds to 1-2 percent of the yeast medium protein.

When this medium HGH was purified by antibody affinity chromatography (Hybritech Ab) and HPLC as used for the interferons, NH$_2$-terminal sequencing showed that nearly 100 percent of the HGH was mature HGH (sequencing was done for 10 residues) as shown in part in FIG. 13. Thus, all of the medium HGH is processed faithfully as is done by human cells.

Notwithstanding that reference has been made to particular preferred embodiments, it will be further understood that the present invention is not to be construed as limited to such, rather to the lawful scope of the appended claims.

Bibliography

1. Novick, P., Field, C., and Schekman, *Cell* 21, 205-215 (1980).
2. Duntze, et al., *Science* 168, 1472 (1970).
3. Woods, et al., *J. Gen. Microbiol.* 51, 115 (1968).
4. Cabib, et al., *J. Bacteriology* 124, 1586 (1975).
5. Farkas, *Microbiol. Rev* 43, 117 (1979).
6. Moor, *Arch. Mikrobiol.* 57, 135 (1967).
7. Goeddel, et al., *Nature* 287, 411 (1980).
8. Goeddel, et al., *Nature* 290, 20 (1981).
9. Yelverton, et al., *Nucleic Acids Research* 9, 731 (1981).
10. Goeddel, et al., *Nucleic Acids Research* 8, 4057 (1980).
11. Wetzel, *American Scientist* 68, 664 (1980).
12. Wetzel, et al., *Biochemistry* 19, 6096 (1980).
13. Davis, et al., *Proc. Natl. Acad. Sci. (USA)* 78, 5376 (1981).
14. Hitzeman, et al., *Nature* 293, 717 (1981).
15. Kleid, et al., *Science* 214, 1125 (1981).
16. Lawn, et al., *Nucleic Acids Res.* 9, 6103 (1981).
17. Weck, et al., *Nucleic Acids Res.* 9, 6153 (1981).
18. Clarke, L. and Carbon, J. *Cell* 9, 91-99 (1976).
19. Clarke, L. and Carbon, J. *PNAS* 72, 4361-4365 (1975).
20. Birnboim, H. C., and Doly, J. *Nucleic Acids Res.* 7, 1513-1523 (1979).
21. Hinnen, A., Hicks, J. B., and Fink, F. R. *Proc. Natl. Acad. Sci. USA* 75, 1929-1933 (1978).
22. Backman, K., Ptashne, M., and Gilbert, W., *Proc. Natl. Acad. Sci. USA* 73, 4174-4178 (1976).
23. Jones E. *Genetics* 85, 23 (1976).
24. Faye, G., Leung, D. W., Tachell, K., Hall, B. D., and Smith, M. *Proc. Natl. Acad. Sci. USA* 78, 2258-2262 (1981).
25. Miller, J. H., *Experiments in Molecular Genetics*, pp. 431-433, Cold Spring Harbor Laboratory, Cold Spring Harbor, NY.
26. Stewart, W. E. II *The Inteferon System* (Springer, New York, 1979).
27. P. Edman, G. Begg, "A Protein Sequencer" *Eur. J. Biochem.*, 1, 80-91 (1967).
8. Tarr, G. E., Beecher, J. F. Bell, M. and McKean, D. J. *Anal. Biochem.* 84, 622-627, (1978).
29. Wittmann-Liebold, B., Graffunder, H., and Kohls, H. *Anal. Biochem.* 75, 621-633 (1976).
30. Gray, P. W., et al., *Nature* 295, 503-508 (1982).
31. Emr, S. D., et al., *Nature* 285, 82-85 (1980).
32. Novick, P. and Schekman. *Proc. Natl. Acad. Sci. USA* 76, 1858-1862 (1979).
33. Bolivar, F., Rodriguez, R. L, Green, P. Y., Betlach, M. C., Heyneker, H. L., Boyer, H. W., Crosa, Y. H., and Falkow, S. *Gene* 2, 95-113 (1977).
34. Stinchcomb, D. T., Struhl, K., and Davis, R. W. *Nature* 282, 39-43 (1979).
35. Kingsman, A. J., Clarke, L., Mortimer, R., and Carbon, J. *Gene* 7, 141-153 (1979).
36. Tschumper, G., and Carbon, J. *Gene* 10, (1980).
37. Hartley, J. L. and Donelson, J. E. *Nature* 286, 860-865 (1980).
37a. Hitzeman, R. A., Clarke, L., and Carbon, J. *J. Biol. Chem.* 255, 12073 (1980).
37b. Broach et al., *Gene* 8, 121 (1979).
38. Messing, et al., *Nucleic Acids Research* 9, 309 (1981).
9. Maxam, A. M., and Gilbert, W. *Methods in Enzymol.* 65, 490-565 (1980).
40. Crea, R. and Horn, T. *Nucleic Acids Res.* 8, 2331-2348.
41. Oakley, B. R. et al., *Anal. Biochem.* 105, 361 (1980).
42. Goodman, H. M., et al. in *Specific Eukaryotic Genes* (Eds. Engberg, J., Klenow, H., and Leick, V.) 179-190 (Munskagaard, Copenhagen, 1979).
43. DeBoer, H., et al. in *Promoters: Structure and Function* (eds. Prayer) pp. 468-481 (1982).
44. Goeddel, D. V. et al., *Nature* 281, 544 (1979).
45. Bennetzen, J. L., and Hall, B. D., *J. Biol. Chem.* 257, 3026 (1982).
46. Ames, G. F.-L., *J. Biol. Chem.* 249, 634 (1974).
47. Towbin, H. et al., *Proc. Natl. Acad. Sci.* 76, 4350 (1979).

We claim:

1. A yeast organism cell culture capable of expressing, processing and secreting a protein heterologous to said yeast organism comprising (1) viable yeast cells transformed with an expression vehicle functionally containing DNA encoding said protein together with a heterologous signal polypeptide therefor, said heterologous signal not being normally produced or employed by said yeast organism, and (2) a medium supporting said cell culture, said medium containing said protein as a product of said yeast organism expression, processing and secretion.

2. A cell culture according to claim 1 wherein the yeast organism is *Saccharomyces cerevisiae*.

3. A yeast organism cell culture capable of expressing, processing and secreting a protein heterologous to said yeast organism comprising (1) viable yeast cells transformed with an expression vehicle functionally containing DNA encoding said protein together with a heterologous signal polypeptide therefor, wherein said heterologous signal polypeptide is a hybrid of a signal native to said protein and of a second heterologous signal polypeptide and (2) a medium supporting said cell culture, said medium containing said protein as a product of said yeast organism expression, processing and secretion.

4. A yeast expression vehicle functionally containing DNA encoding a protein heterologous to a yeast organism and a heterologous signal polypeptide in translationl reading frame with the DNA encoding the heterologous protein wherein said heterologous signal polypeptide is a hybrid of a signal native to said protein and of a second heterologous signal polypeptide.

5. A process for obtaining protein heterologous to a yeast organism as a product of yeast expression, processing and secretion comprising (a) providing an expression vehicle functionally containing DNA encoding said protein and a heterologous signal peptide, said heterologous signal not being normally produced or employed by said yeast organism, (b) transforming with the expression vehicle a yeast organism capable of expressing and processing the protein and heterologous signal peptide and secreting the heterologous protein, (c) preparing a culture of said organism, (d) growing the culture and (e) recovering said protein from the medium of said culture.

6. The process of claim 5 wherein the recovered heterologous protein is separated from forms of the protein having additional amino acids of the heterologous signal polypeptide.

7. The process of claim 6 wherein the heterologous protein is human growth hormone.

8. The process of claim 5 wherein the heterologous protein is recovered from the culture medium when the culture has reached stationary phase.

9. The process of claim 5 wherein the vehicle contains tandem copies of DNA encoding the heterologous protein.

10. The process of claim 5 wherein the heterologous protein is a human protein.

11. The process of claim 5 wherein the heterologous protein is human serum albumin.

12. The process of claim 5 wherein the yeast organism is *Saccharomyces cerevisiae* and the protein is human growth hormone.

13. The process of claim 5 wherien the protein is a glycoprotein.

14. The process of claim 5 wherein the protein is a hormone, viral antigen, human serum albumin, human insulin or a glycoprotein.

15. A process for obtaining protein heterologous to a yeast organism as a product of yeast expression, processing and secretion comprising providing an expression vehicle functionally containing DNA encoding said protein and a heterologous signal peptide native to the heterologous protein, transforming with the expression vehicle a yeast organism capable of expressing and processing the protein and heterologous signal peptide and secreting the heterologous protein, preparing a culture of said organism, growing the culture, and recovering said protein from the medium of said culture.

16. A process for obtaining protein heterologous to a yeast organism as a product of yeast expression, processing and secretion comprising providing an expression vehicle functionally containing DNA encoding said protein and a heterologous signal peptide which is not from a baterial source, said heterologous signal not being normally produced or employed by said yeast organism, transforming with the expression vehicle a yeast organism capable of expressing and processing the protein and heterologous signal peptide and secreting the heterologous protein, preparing a culture of said organism, growing the culture and recovering said protein from the medium of said culture.

17. A yeast organism culture comprising (a) a yeast organism transformed with a yeast expression vehicle functionally containing DNA encoding a protein heterologous to the yeast organism and DNA encoding a heterologous signal polypeptide, said heterologous signal not being normally produced or employed by said yeast organism, and (b) culture medium containing said heterologous protein in mature form as a product of yeast secretion of the mature heterologous protein produced upon growth of the yeast organism in culture medium.

18. A yeast expression vehicle replicable in *E. coli* or in *Saccharomyces cerevisiae*, which vehicle contains DNA encoding a heterologous signal polypeptide in translational reading frame with DNA encoding said heterologous protein, wherein said signal polypeptide is a hybrid of a signal native to said protein and of a second heterologous signal polypeptide wherein said heterologous protein is expressed and secreted from a *Saccharomyces cerevisiae* host cell transformed with said vehicle.

19. A process for obtaining mature human growth hormone comprising transforming a yeast organism with an expression vehicle functionally containing DNA encoding pre human growth hormon wherein said yeast organism is capable of expressing and processing pre human growth hormone and secreting mature human growth hormone, preparing a culture of said yeast organism, growing the culture and recovering mature human growth hormone from the medium.

* * * * *